(12) United States Patent
Mohapatra et al.

(10) Patent No.: US 10,813,935 B2
(45) Date of Patent: Oct. 27, 2020

(54) METHODS AND COMPOSITIONS FOR TREATING DRUG RESISTANCE IN CANCER

(71) Applicants: UNIVERSITY OF SOUTH FLORIDA, Tampa, FL (US); TRANSGENEX NANOBIOTECH, INC., Lutz, FL (US)

(72) Inventors: Subhra Mohapatra, Lutz, FL (US); Shyam S. Mohapatra, Lutz, FL (US); Mark Howell, Tampa, FL (US); Rajesh Nair, Tampa, FL (US)

(73) Assignees: TRANSGENEX NANOBIOTECH, INC., Lutz, FL (US); University of South Florida, Tampa, FL (US)

( * ) Notice: Subject to any disclaimer, the term of this patent is extended or adjusted under 35 U.S.C. 154(b) by 0 days.

(21) Appl. No.: 15/904,176

(22) Filed: Feb. 23, 2018

(65) Prior Publication Data
US 2018/0256579 A1 Sep. 13, 2018

Related U.S. Application Data

(60) Provisional application No. 62/462,812, filed on Feb. 23, 2017.

(51) Int. Cl.
*A61K 31/517* (2006.01)
*A61P 35/00* (2006.01)
*A61K 31/496* (2006.01)

(52) U.S. Cl.
CPC ......... *A61K 31/517* (2013.01); *A61P 35/00* (2018.01); *A61K 31/496* (2013.01); *A61K 2300/00* (2013.01)

(58) Field of Classification Search
CPC .... A61K 2300/00; A61K 31/496; A61P 35/00
USPC ..... 435/6.1, 91.1, 91.31, 455, 458; 514/1, 2, 514/44 A; 536/23.1, 24.5
See application file for complete search history.

(56) References Cited

U.S. PATENT DOCUMENTS

| | | | |
|---|---|---|---|
| 4,554,101 A | 11/1985 | Hopp | |
| 4,870,287 A | 9/1989 | Cole et al. | |
| 5,580,859 A | 12/1996 | Felgner et al. | |
| 5,676,646 A | 10/1997 | Hofmann et al. | |
| 5,679,647 A | 10/1997 | Carson et al. | |
| 5,702,359 A | 12/1997 | Hofmann et al. | |
| 5,703,055 A | 12/1997 | Felgner et al. | |
| 5,760,395 A | 6/1998 | Johnstone | |
| 6,068,650 A | 5/2000 | Hofmann et al. | |
| 6,096,020 A | 8/2000 | Hofmann | |
| 6,120,493 A | 9/2000 | Hofmann | |
| 6,150,148 A | 11/2000 | Nanda et al. | |
| 6,181,964 B1 | 1/2001 | Hofmann et al. | |
| 6,192,270 B1 | 2/2001 | Hofmann et al. | |
| 6,208,893 B1 | 3/2001 | Hofmann | |
| 6,216,034 B1 | 4/2001 | Hofmann et al. | |
| 6,233,482 B1 | 5/2001 | Hofmann et al. | |
| 6,241,701 B1 | 6/2001 | Hofmann | |
| 6,302,874 B1 | 10/2001 | Zhang et al. | |
| 7,664,545 B2 | 2/2010 | Westersten et al. | |
| 2015/0152474 A1* | 6/2015 | Pawlowski | C12Q 1/6886 506/4 |
| 2019/0000763 A1* | 1/2019 | Pilgaonkar | A61K 9/5031 |

OTHER PUBLICATIONS

Fan et al, Cancer Res., vol. 71, No. 13, pp. 4494-4505 (Year: 2011).*
Wang et al, J. Hematology and Oncology, vol. 9, No. 34, pp. 1-7 (Year: 2016).*
Janne et al, NEJM, vol. 372, No. 18, pp. 1689-1699 (Year: 2015).*
American Cancer Society, Cancer Facts and Figures 2017.
C.T.F.A. Cosmetic Ingredient Handbook, 1992, pp. 587-592.
Costa et al., "Whacking a mole-cule: clinical activity and mechanisms of resistance to third generation EGFR inhibitors in EGFR mutated lung cancer with EGFR-T790M," Transl Lung Cancer Res, 2015, 4(6): 809-815.
Donnelly et al., "DNA vaccines," Ann. Rev. Immunol., 1997, 15:617-648.
Fan et al., "MET-independent lung cancer cells evading EGFR kinase inhibitors are therapeutically susceptible to BH3 mimetic agents," Cancer Res, 2011, 71(3): 4494-4505.
Girard et al., "A 3D fibrous scaffold inducing tumoroids: a platform for anti-cancer drug development," PloS one, 2013. 8(10): e75345.
Heagerty et al., "Time-dependent ROC curves for censored survival data and a diagnostic marker," Biometrics, 2000, 56(2):337-44.
Howell et al., "Mechanism of Treatment-induced Drug Resistance in Lung Cancer," 2017.
Janne et al., "AZD9291 in EGFR inhibitor-resistant non-small-cell lung cancer," N Engl J Med, 2015, 372(18): 1689-1699.

(Continued)

*Primary Examiner* — Jane J Zara
(74) *Attorney, Agent, or Firm* — Fish & Richardson P.C.

(57) ABSTRACT

Disclosed herein are compositions and methods for treating cancer. Further provided herein are compositions and methods for reducing, inhibiting, or preventing resistance of cancer to tyrosine kinase inhibitors. The methods may include administering an anti-resistance agent such as a CYP51A1 inhibitor or an agonist of miRNA-764 (SEQ ID NO: 4) to a subject. A tyrosine kinase inhibitor may also be administered to the subject in addition to the anti-resistance agent.

12 Claims, 5 Drawing Sheets

Specification includes a Sequence Listing.

(56) References Cited

OTHER PUBLICATIONS

Kyle et al., "A simple method for displaying the hydropathic character of a protein," J. Mol. Biol., 1982, 157(1):105-132.
McCutcheon's vol. 1, Emulsifiers & Detergents, 1994, North American Edition, pp. 236-239.
Remington's Pharmaceutical Sciences, 15th Ed. 1975, pp. 335-337.
Song et al., "Dual inhibition of MEK1/2 and EGFR synergistically induces caspase-3-dependent apoptosis in EGFR inhibitor-resistant lung cancer cells via BIM upregulation," Invest New Drugs, 2013, 31(6): 1458-1465.
Wang et al., "Mechanisms of resistance to third-generation EGFR tyrosine kinase inhibitors," Front Med, 2016, 10(4): 383-388.
Wang, et al., "Third-generation inhibitors targeting EGFR T790M mutation in advanced non-small cell lung cancer," J Hematol Oncol, 2016, 9: p. 34.
Wheeler et al., "Understanding resistance to EGFR inhibitors-impact on future treatment strategies," Nat Rev Clin Oncol, 2010, 7(9): 493-507.
Yver, "Osimertinib (AZD9291)-ascience-driven, collaborative approach to rapid drug design and development," Ann Oncol, 2016, 27(6): 1165-1170.

\* cited by examiner

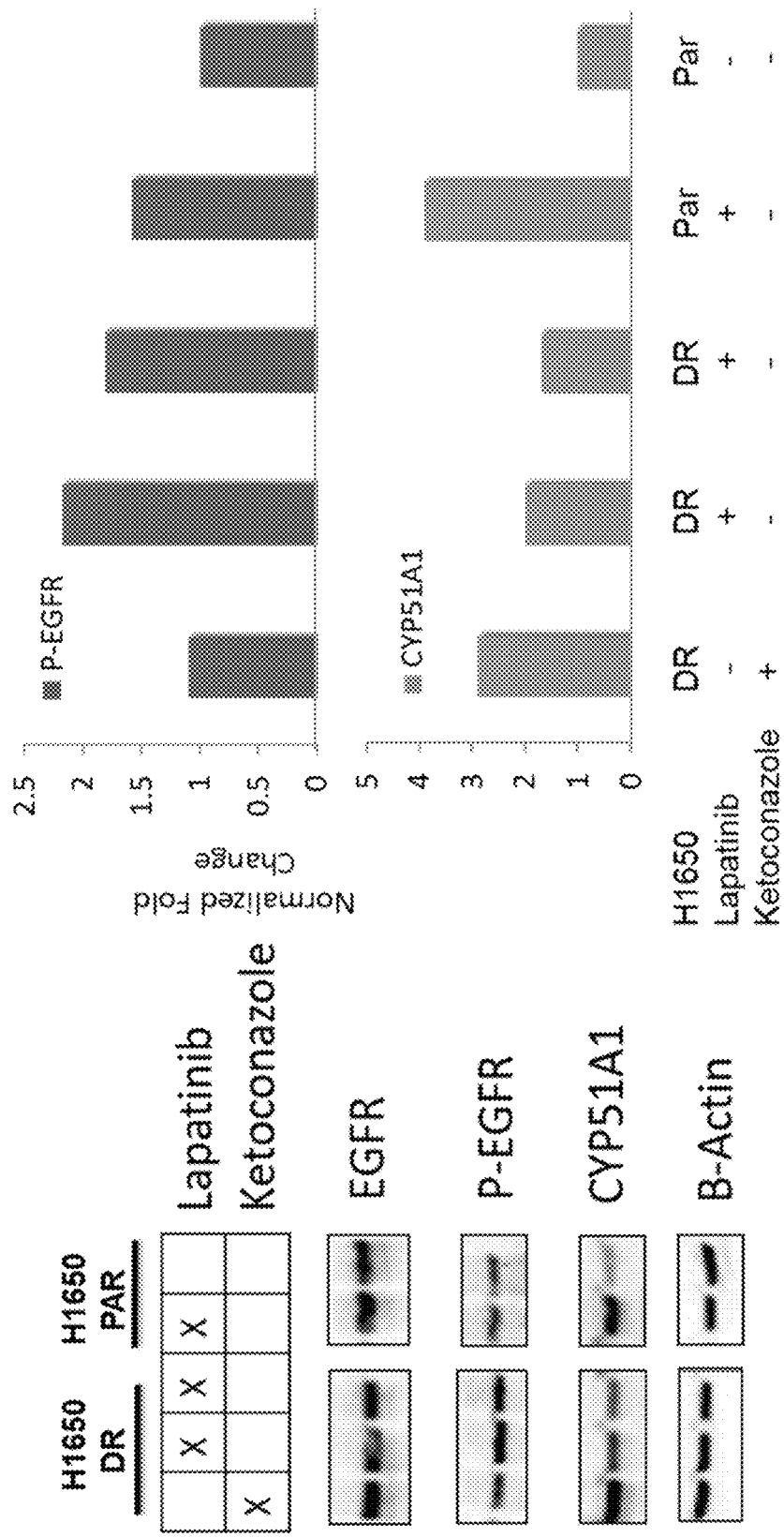

METHODS AND COMPOSITIONS FOR TREATING DRUG RESISTANCE IN CANCER

CROSS-REFERENCE TO RELATED APPLICATION(S)

This application claims priority to U.S. Provisional Patent Application No. 62/462,812, filed Feb. 23, 2017, which is incorporated herein by reference in its entirety.

STATEMENT REGARDING FEDERALLY SPONSORED RESEARCH

This invention was made with government support under grants R01CA152005, HHSN261201400022C, and HHSN261201300044C awarded by the National Cancer Institute (NCI) of the National Institutes of Health (NIH). The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,492 Bytes ASCII (Text) file named "17A023PRC-210112-9029-US02_ST25.txt", created on May 21, 2018.

FIELD

This disclosure relates to cancer therapies, as well as preventing or reducing drug resistance in cancer.

INTRODUCTION

Lung cancer is the number one cause of cancer related death in both males and females. About 20% of all non-small cell lung cancer (NSCLC) patients are expected to harbor an epidermal growth factor receptor (EGFR) activating mutation. EGFR inhibitors have been shown to provide clinical benefits over chemotherapy for lung cancer patients with EGFR activating mutations. First- and second-generation EGFR tyrosine kinase inhibitors (TKIs) are clinically approved to treat advanced NSCLC patients. However, despite the initial clinical responses to these EGFR targeted therapies, long-term efficacy is currently not possible because acquired drug resistance to the EGFR inhibitors hampers the effectiveness of these therapies. Effective treatments are yet to be discovered.

SUMMARY

In an aspect, the disclosure relates to methods of treating cancer in a subject. The methods may include administering to the subject a tyrosine kinase inhibitor and an anti-resistance agent. In some embodiments, the tyrosine kinase inhibitor and the anti-resistance agent are co-administered to the subject. In some embodiments, the tyrosine kinase inhibitor is administered to the subject prior to the anti-resistance agent. In some embodiments, the anti-resistance agent is administered to the subject prior to the tyrosine kinase inhibitor.

In a further aspect, the disclosure relates to methods of treating cancer in a subject undergoing treatment with a tyrosine kinase inhibitor. The methods may include administering to the subject an anti-resistance agent. In some embodiments, the cancer is a tyrosine kinase inhibitor-resistant cancer.

Another aspect of the disclosure provides methods for preventing drug resistance or enhancing the therapeutic efficacy of a tyrosine kinase inhibitor in a subject having cancer and undergoing treatment with the tyrosine kinase inhibitor. The methods may include administering to the subject a pharmaceutical composition comprising an anti-resistance agent in an amount effective to attenuate resistance to the tyrosine kinase inhibitor.

Another aspect of the disclosure provides methods of sensitizing a tyrosine kinase inhibitor-resistant cancer in a subject to the tyrosine kinase inhibitor. The methods may include administering to the subject an anti-resistance agent.

In some embodiments, the anti-resistance agent comprises a CYP51A1 inhibitor, or an agonist of SEQ ID NO: 4 (miRNA-764), or a combination thereof. In some embodiments, the anti-resistance agent comprises a CYP51A1 inhibitor. In some embodiments, the CYP51A1 inhibitor comprises ketoconazole. In some embodiments, the anti-resistance agent comprises an agonist of SEQ ID NO: 4 (miRNA-764). In some embodiments, the anti-resistance agent comprises a polynucleotide having a sequence of SEQ ID NO: 4 (miRNA-764). In some embodiments, the cancer comprises non-small cell lung cancer (NSCLC). In some embodiments, acquired drug resistance to the tyrosine kinase inhibitor is decreased or prevented. In some embodiments, tyrosine kinase inhibitor resistance is decreased at least 2-fold. In some embodiments, tyrosine kinase inhibitor resistance is decreased at least 5-fold. In some embodiments, the activity of the tyrosine kinase inhibitor is increased at least 2-fold. In some embodiments, the activity of the tyrosine kinase inhibitor is increased at least 5-fold. In some embodiments, tyrosine kinase inhibitor comprises lapatinib.

The disclosure provides for other aspects and embodiments that will be apparent in light of the following detailed description and accompanying figures.

BRIEF DESCRIPTION OF THE DRAWINGS

FIG. 3A, FIG. 3B, and FIG. 3C are images, gels, and graphs of an analysis of drug-resistant cells compared to parental cell lines. Shown in FIG. 3A are 500,000 H1650 cells that were plated in 1 well of a 6-well plate and treated with the indicated drugs at the time of plating and allowed to grow for 72 hours. Microscopy pictures were taken using bright field microscopy at 100×. Shown in FIG. 3B is a Western blot analysis of the expression of cleaved EGFR, p-EGFR, and CYP51A1 from whole cell lysates, showing that ketoconazole induced lowering of EGFR downstream signaling. Cells were treated with lapatinib or ketoconazole for 48 hours. β-Actin was included as a loading control. FIG. 3C are graphs of the densitometry of the western blot bands, as performed using ImageJ software.

DETAILED DESCRIPTION

Figure 1:
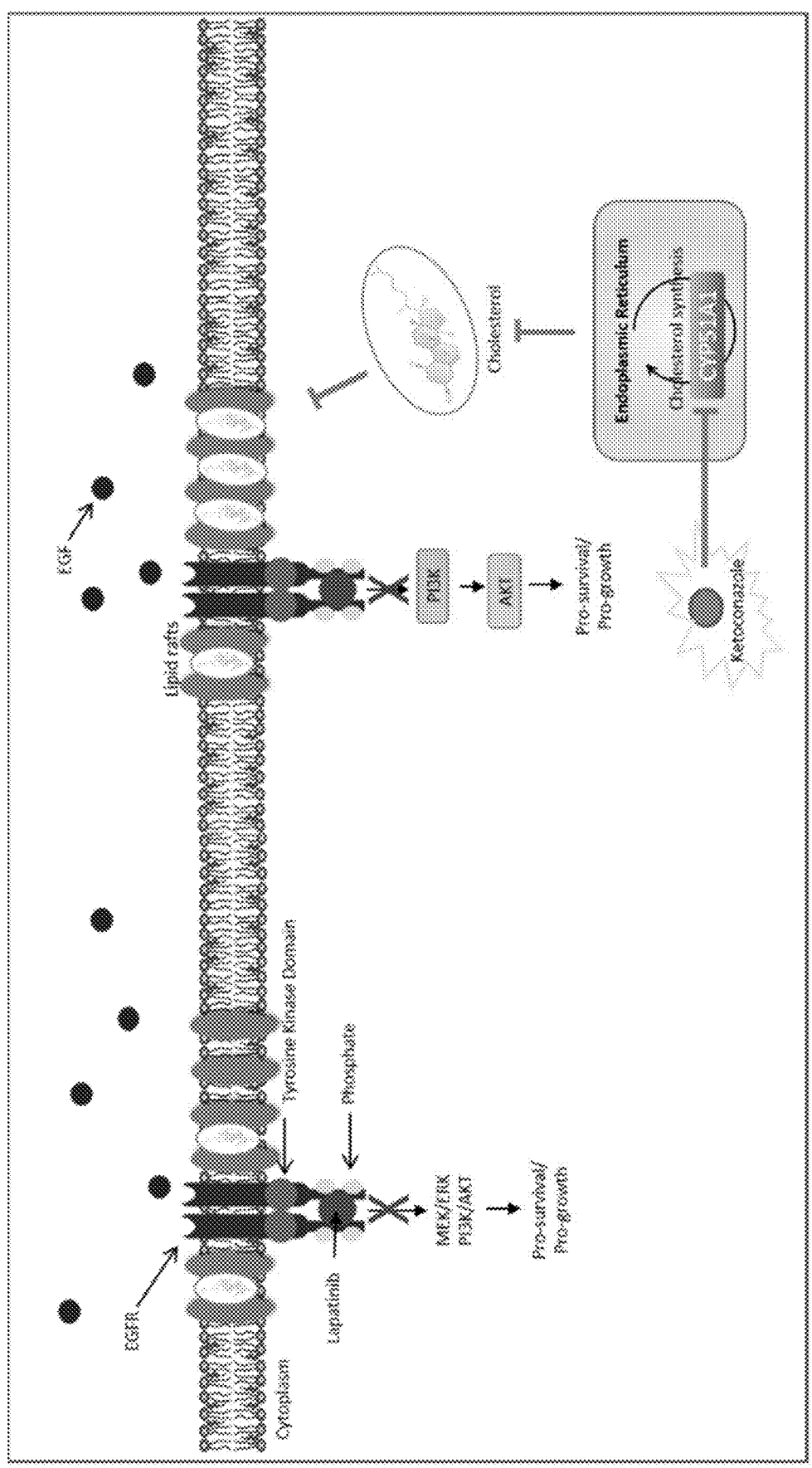
FIG. 1 is a schematic of the proposed mechanism of action for ketoconazole.

Described herein are methods and compositions for treating cancer, and for preventing resistance to an antiproliferative drug or enhancing its therapeutic effect in a subject. Using multi-drug resistant cell lines and a 3D culture platform, we have found that treatment with an inhibitor of CYP51A1 can sensitize drug resistant cancer to continued treatment with the drug. We have also discovered that miR-764 (SEQ ID NO: 4) is downregulated in multi-drug resistant cancer cell lines. Inhibitors of CYP51A1 and/or agonists of miR-764 (SEQ ID NO: 4) may be used alone or in combination with an antiproliferative drug to prevent acquired resistance to the antiproliferative drug. Overexpression of miR-764 (SEQ ID NO: 4) or inhibition of CYP51A1 can be used as therapeutics to sensitize drug resistant cancers and/or prevent acquired drug resistance.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration" or "administering," as used herein, refers to providing, contacting, and/or delivery of an agent by any appropriate route to achieve the desired effect. These agents may be administered to a subject in numerous ways including, but not limited to, orally, ocularly, nasally, intravenously, topically, as aerosols, suppository, etc. and may be used in combination.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "agonist" refers to a biologically active ligand that binds to its complementary biologically active receptor and activates the receptor either to cause a biological response in the receptor or to enhance a biological activity of the receptor. An agonist may trigger (e.g., initiate or promote), partially or fully enhance, stimulate, increase, or activate one or more biological activities. An agonist may mimic the action of a naturally occurring substance. Whereas an agonist causes an action, an antagonist blocks the action of the agonist.

"Antagonist" or "inhibitor" may be used interchangeably and refers to an agent that inhibits the effect of an agonist. An antagonist may be a compound that inhibits or reduces an activity of a polypeptide. An antagonist may indirectly or directly bind a polypeptide and inhibit the activity of the polypeptide, including binding activity or catalytic activity. For example, an antagonist may prevent expression of a polypeptide, or inhibit the ability of a polypeptide to mediate the binding of the polypeptide to a ligand. An "allosteric antagonist" refers to a compound that binds to a polypeptide at a secondary site, distinct from the primary ligand binding site, and inhibits or reduces an activity of the polypeptide. The terms "inhibit" or "inhibiting" mean that an activity is decreased or prevented in the presence of an inhibitor as opposed to in the absence of the inhibitor. The term "inhibition" refers to the reduction or down regulation of a process or the elimination of a stimulus for a process, which results in the absence or minimization of the expression or activity of a biomolecule or polypeptide. Inhibition may be direct or indirect. Inhibition may be specific, that is, the inhibitor inhibits a biomolecule or polypeptide and not others.

"Cancer" refers to a neoplasm or tumor resulting from abnormal and uncontrolled growth of cells. Cancer may also be referred to as a cellular-proliferative disease. Cancer may include different histological types, cell types, and different stages of cancer, such as, for example, primary tumor or metastatic growth. Cancer may include, for example, breast cancer, cholangiocellular carcinoma, colorectal cancer, endometriosis, esophageal cancer, gastric cancer, diffused type gastric cancer, pancreatic cancer, renal carcinoma, soft tissue tumor, testicular cancer, cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma, non-small cell lung cancer (NSCLC), small cell lung cancer (SCLC); Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma, glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian cancer, ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma], CML; Skin: melanoma, malignant melanoma, basal cell carcinoma, squamous cell carcinoma, Karposi's sarcoma, moles, dysplastic nevi, lipoma, angioma, dermatofibroma, keloids, psoriasis; and Adrenal glands: neuroblastoma. In some embodiments, the cancer comprises non-small cell lung cancer (NSCLC). In some embodiments, the cancer is resistant to a therapy. In some embodiments, the cancer is not resistant to a therapy.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, diseased after treatment, or healthy after treatment, or a combination thereof. The term "normal subject" as used herein means a healthy subject, i.e. a subject having no clinical signs or symptoms of disease. The normal subject is clinically evaluated for otherwise undetected signs or symptoms of disease, which evaluation may include routine physical examination and/or laboratory testing. In some embodiments, the control is a healthy control. In some embodiments, the control comprises cancer.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

Polynucleotides are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a polynucleotide sequence, even if internal to a larger oligonucleotide, also may be said to have 5' and 3' ends. In either a linear or circular polynucleotide, discrete elements are referred to as being "upstream" or 5' of the "downstream" or 3' elements. This terminology reflects the fact that transcription proceeds in a 5' to 3' fashion along the polynucleotide strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "gene" means the polynucleotide sequence comprising the coding region of a gene, e.g., a structural gene, and the including sequences located adjacent to the coding region on both the 5' and 3' ends for a distance of about 1 kb on either end such that the gene corresponds to the length of the full-length mRNA. The sequences which are located 5' or upstream of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA, for example, heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, an oligonucleotide or polynucleotide "having a nucleotide sequence encoding a gene" means a polynucleotide sequence comprising the coding region of a gene, or in other words, the nucleic acid sequence which encodes a gene product. The coding region may be present in either a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the vector may contain endogenous enhancers/promoters, splice junctions, intervening sequences, polyadenylation signals, etc., or a combination of both endogenous and exogenous control elements.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, for example, enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be, for example, 2 to 20, 2 to 15, or 2 to 10 amino acids in length. In some embodiments, a motif includes 3, 4, 5, 6, or 7 sequential amino acids. A domain may be comprised of a series of the same type of motif.

"Recombinant" when used with reference, for example, to a cell, nucleic acid, polynucleotide, protein, or vector, indicates that the cell, nucleic acid, polynucleotide protein, or vector, has been modified by the introduction of a heterologous nucleic acid or protein or the alteration of a native polynucleotide or protein, or that the cell is derived from a cell so modified. Thus, for example, recombinant cells express genes that are not found within the native (non-recombinant) form of the cell or express native genes that are otherwise abnormally expressed, under expressed, or not expressed at all. For example, the term "recombinant DNA molecule" as used herein refers to a DNA molecule which is comprised of segments of DNA joined together by means of molecular biological techniques. The term "recombinant protein" or "recombinant polypeptide" as used herein refers to a protein molecule which is expressed from a recombinant DNA molecule or recombinant polynucleotide.

The term "specificity" as used herein refers to the number of true negatives divided by the number of true negatives plus the number of false positives, where specificity ("spec") may be within the range of $0<\text{spec}<1$. Hence, a method that has both sensitivity and specificity equaling one, or 100%, is preferred.

By "specifically binds," it is generally meant that an agent or polypeptide binds to a target when it binds to that target more readily than it would bind to a random, unrelated target.

"Sample" or "test sample" as used herein can mean any sample in which the presence and/or level of an activity, a biomarker, target, agent, vector, or molecule, etc., is to be detected or determined. Samples may include liquids, solutions, emulsions, mixtures, or suspensions. Samples may include a medical sample. Samples may include any biological fluid or tissue, such as blood, whole blood, fractions of blood such as plasma and serum, peripheral blood mononuclear cells (PBMCs), muscle, interstitial fluid, sweat, saliva, urine, tears, synovial fluid, bone marrow, cerebrospinal fluid, nasal secretions, sputum, amniotic fluid, bronchioalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a subject or can be pre-treated, such as by filtration, distillation, extraction, concentration, centrifugation, inactivation of interfering components, addition of reagents, and the like, to modify the character of the sample in some manner as discussed herein or otherwise as is known in the art. Samples may be obtained before treatment, before diagnosis, during treatment, after treatment, or after diagnosis, or a combination thereof.

"Subject" as used herein can mean an organism that wants or is in need of the herein described compositions or methods. The subject may be a human or a non-human animal. The subject may be a microorganism. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

In some embodiments, the subject is human. In some embodiments, the subject has a specific genetic marker.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides, respectively.

A "therapeutically effective amount," or "effective dosage," or "effective amount" as used interchangeably herein unless otherwise defined, means a dosage of an agent or drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in a subject. A therapeutically effective amount may be administered in one or more administrations (e.g., the composition may be given as a preventative treatment or therapeutically at any stage of disease progression, before or after symptoms, and the like), applications, or dosages, and is not intended to be limited to a particular formulation, combination, or administration route. It is within the scope of the present disclosure that the drug may be administered at various times during the course of treatment of the subject. The times of administration and dosages used will depend on several factors, such as the goal of treatment (e.g., treating v. preventing), condition of the subject, etc. and can be readily determined by one skilled in the art. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment. The terms "treat," "treated," or "treating" may include preventing, suppressing, repressing, ameliorating, or completely eliminating the disease. Preventing the disease may involve administering a composition of the present invention to a subject prior to onset of the disease. Suppressing the disease may involve administering a composition of the present invention to a subject after induction of the disease but before its clinical appearance. Repressing or ameliorating the disease may involve administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof.

The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof. In some embodiments, variants include homologues. Homologues may be polynucleotides or polypeptides or genes inherited in two species by a common ancestor.

2. TYROSINE KINASE

A tyrosine kinase is an enzyme that can transfer a gamma (terminal) phosphate group from ATP to a polypeptide in a cell. The phosphate group is attached to the amino acid tyrosine on the polypeptide. The tyrosine kinase may phosphorylate one or more tyrosine residues on a polypeptide. The phosphorylation of the tyrosine on the polypeptide can cause a change in the function of the polypeptide. Tyrosine kinases are a subgroup of the larger class of protein kinases that attach phosphate groups to other amino acids (such as serine and threonine). Phosphorylation of proteins by kinases is one mechanism in communicating signals within a cell (signal transduction) and regulating cellular activity, such as cell division.

The epidermal growth factor receptor (EGFR; ErbB-1; HER1 in humans) is a member of the ErbB family of receptors, which is a subfamily of four closely related receptor tyrosine kinases. The ErbB family of receptors includes EGFR (ErbB-1; HER1), HER2/neu (ErbB-2), HER3 (ErbB-3), and HER4 (ErbB-4). EGFR is a transmembrane protein that is a receptor for members of the epidermal growth factor family (EGF family) of extracellular protein ligands. EGFR is activated by binding of its specific ligands, the ligands including epidermal growth factor (EGF) and transforming growth factor α (TGFα). Upon activation by its ligands, EGFR may transition from an inactive monomeric form to an active homodimer. In addition to forming homodimers after ligand binding, EGFR may pair with another member of the ErbB receptor family, such as ErbB2/Her2/neu, to create an activated heterodimer. EGFR dimerization may stimulate its intrinsic intracellular protein-tyrosine kinase activity. As a result, autophosphorylation of several tyrosine residues in the C-terminal domain of EGFR may occur. These tyrosine residues may include Y992, Y1045, Y1068, Y1148 and Y1173. The autophosphorylation of EGFR may elicit downstream activation and signaling by several other polypeptides that associate with the phosphorylated tyrosines through their own phosphotyrosine-binding SH2 domains. These downstream signaling polypeptides may initiate several signal transduction cascades, such as the MAPK, Akt and JNK pathways. The signal transduction cascades may lead to cellular activities such as DNA synthesis, cell proliferation, cell migration, and cell adhesion. The kinase domain of EGFR may also cross-phosphorylate tyrosine residues of other receptors it is aggregated with, and EGFR can itself be cross-phosphorylated and activated by a kinase domain of a receptor it is aggregated with.

Mutations affecting EGFR expression or activity may result in cancer. For example, mutations leading to over-expression of EGFR are associated with the development of a wide variety of cancers. Over-expression of EGFR or constant activation of EGFR may produce uncontrolled cell division.

a. Tyrosine Kinase Inhibitors

A tyrosine kinase inhibitor (TKI) inhibits the activity or expression of a tyrosine kinase. A tyrosine kinase inhibitor may include an antibody, a polynucleotide such as interfering RNA, a small molecule, or a combination thereof. In some embodiments, the tyrosine kinase inhibitor comprises an antibody. In some embodiments, the antibody is a monoclonal antibody. In some embodiments, the tyrosine kinase inhibitor comprises a small molecule. The tyrosine kinase inhibitor may be specific for a particular tyrosine kinase, or for a particular family or subfamily of tyrosine kinases. In some embodiments, the tyrosine kinase inhibitor is specific for EGFR. Such inhibitors may be referred to as "EGFR inhibitors." Antibody EGFR inhibitors include, for example, cetuximab and panitumumab. Small molecule EGFR inhibitors include, for example, lapatinib (a mixed EGFR and ERBB2 inhibitor), mereletinib (osimertinib), gefitinib, icotinib, erlotinib, afatinib, and brigatinib. In some embodiments, the EGFR inhibitor comprises lapatinib. The EGFR inhibitor may bind and inhibit the kinase domain of the EGFR. Without kinase activity, the EGFR may not be able to activate itself or induce downstream activation and signaling.

3. ANTI-RESISTANCE AGENT

Further provided herein is an anti-resistance agent. The anti-resistance agent may reduce or prevent resistance of a cancer to a tyrosine kinase inhibitor. The anti-resistance agent may be, for example, an antibody, a polynucleotide, a small molecule, or a combination thereof. The anti-resistance agent may cause target alteration, increase or decrease ligand production or availability, increase or decrease downstream pathway activation, or activate or inhibit an alternative pathway, or a combination thereof, to reduce or prevent resistance of a cancer to a tyrosine kinase inhibitor. Acquired drug resistance to the tyrosine kinase inhibitor may be decreased or prevented following administration of the anti-resistance agent. Tyrosine kinase inhibitor resistance may be decreased at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold. In some embodiments, tyrosine kinase inhibitor resistance is decreased 2-fold to 10-fold. Tyrosine kinase inhibitor activity may be increased at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold. In some embodiments, tyrosine kinase inhibitor activity is increased 2-fold to 10-fold. Anti-resistance agents may include CYP51A1 inhibitors and agonists of miRNA-764 (SEQ ID NO: 4).

a. CYP51A1 Inhibitor

A CYP51A1 inhibitor inhibits the activity or expression of CYP51A1 (lanosterol 14α-demethylase; Cytochrome P450, Family 51, Subfamily A, Polypeptide 1). CYP51A1 is a cytochrome P450 enzyme that is involved in the conversion of lanosterol to 4,4-dimethylcholesta-8(9),14,24-trien-3β-ol, which is a step in the biosynthesis of sterols. In particular, CYP51A1 catalyzes the removal of the C-14α-methyl group from lanosterol. This demethylation step is an initial checkpoint in the transformation of lanosterol to other sterols that are widely used within the cell. CYP51A1 may comprise a polypeptide having an amino acid sequence of SEQ ID NO: 1. CYP51A1 may be encoded by gene having a polynucleotide sequence of SEQ ID NO: 2, which may be transcribed to an mRNA having a polynucleotide sequence of SEQ ID NO: 3. CYP51A1 inhibitors include, for example, ketoconazole.

b. Agonist of miRNA-764

Further provided herein are agonists of miRNA-764 (SEQ ID NO: 4). Without being bound by theory, it is possible that miRNA-764 (SEQ ID NO: 4) may regulate CYP51A1. miRNA-764 (SEQ ID NO: 4) may regulate CYP51A1 by binding to the 3'-UTR of the CYP51A1 mRNA (SEQ ID NO: 3) and represses translation of the CYP51A1 mRNA. Agonists of miRNA-764 (SEQ ID NO: 4) increase the level or activity of miRNA-764 (SEQ ID NO: 4). In some embodiments, an agonist of miRNA-764 (SEQ ID NO: 4) comprises a polynucleotide of SEQ ID NO: 4.

4. ADDITIONAL CANCER THERAPIES

In some embodiments, the compositions and methods detailed herein may be used in combination with other cancer therapies. These additional cancer therapies may be administered to a subject at the same time, before, or after the anti-resistance agent or tyrosine kinase inhibitor. Additional cancer therapies may include, for example, chemotherapy, radiation, and surgery.

Chemotherapy uses one or more chemotherapeutic agents to kill highly proliferating cells. A chemotherapeutic agent includes a compound or composition that is administered in the treatment of cancer or other hyperproliferative disease. Chemotherapeutic agents may be categorized by their mode of activity within a cell, for example, whether and at what stage they affect the cell cycle. Alternatively, a chemotherapeutic agent may be characterized based on its ability to directly cross-link DNA, to intercalate into DNA, or to induce chromosomal and mitotic aberrations by affecting nucleic acid synthesis. Categories of chemotherapeutic agents include, for example, alkylating agents, antimetabolites, antitumor antibiotics, mitotic inhibitors, and nitrosoureas. Specific chemotherapeutic agents may include, for example, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin, and chlorambucil, and an agonist of any of the above compounds.

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, normal cells are able to repair and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively).

Radiation therapy may include, for example, the use of γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. Radiation therapy may cause a broad range of damage on DNA, on the precursors of DNA, on the replication and repair of DNA, on the assembly and maintenance of chromosomes, or a combination thereof. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. Radiotherapy may also include the use of radiolabeled antibodies to deliver doses of radiation directly to the cancer site (radioimmunotherapy). Once injected into the body, the antibodies may actively seek out the cancer cells, which are destroyed by the cell-killing (cytotoxic) action of the radiation. This approach can minimize the risk of radiation damage to healthy cells.

Surgery may include full or partial removal of a tumor or cancerous tissue. Surgery may also include removal of any surrounding tissue. Surgery may include removal of any tissue anticipated to be at risk of cancer, such as from spreading or metastasis of cancer to the tissue.

5. PHARMACEUTICAL COMPOSITIONS

Further provided herein are pharmaceutical compositions comprising one or more anti-resistance agents. The pharmaceutical compositions may further include one or more tyrosine kinase inhibitors. Also provided herein are pharmaceutical compositions comprising one or more tyrosine kinase inhibitors. The pharmaceutical compositions may be formulated in accordance with standard techniques well known to those skilled in the pharmaceutical art. The pharmaceutical composition may comprise the anti-resistance agent and/or tyrosine kinase inhibitor and a pharmaceutically acceptable carrier. The term "pharmaceutically acceptable carrier," as used herein, means a non-toxic, inert solid, semi-solid or liquid filler, diluent, encapsulating material or formulation auxiliary of any type.

The route by which the disclosed anti-resistance agents and/or tyrosine kinase inhibitors are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of theobroma. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 0.1 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, Pa.) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate. In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include a compound, and a carrier including one or more diluents disclosed above in a capsule comprising gelatin. Granules typically comprise a compound, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compound into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of a compound and 50% to 99.99% of one or more carriers. Compositions for parenteral administration may typically include 0.1% to 10% of a compound and 90% to 99.9% of one or more carriers. Oral dosage forms may include, for example, at least about 5%, or about 25% to about 50% of a compound. The oral dosage compositions may include about 50% to about 95% of carriers, or from about 50% to about 75% of carriers. The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

6. ADMINISTRATION

The anti-resistance agents and/or tyrosine kinase inhibitors as detailed herein, or the pharmaceutical compositions comprising the same, may be administered to a subject. The anti-resistance agents and/or tyrosine kinase inhibitors as detailed herein can be formulated into a composition and administered in dosages and by techniques well known to those skilled in the medical arts taking into consideration such factors as the age, sex, weight, and condition of the particular subject, and the route of administration.

The anti-resistance agents and/or tyrosine kinase inhibitors can be administered prophylactically or therapeutically. In prophylactic administration, the anti-resistance agents and/or tyrosine kinase inhibitors can be administered in an amount sufficient to induce a response. In therapeutic applications, the anti-resistance agents and/or tyrosine kinase inhibitors are administered to a subject in need thereof in an amount sufficient to elicit a therapeutic effect. The anti-resistance agents and/or tyrosine kinase inhibitors may be administered in a therapeutically effective amount.

For example, a therapeutically effective amount of an anti-resistance agent and/or tyrosine kinase inhibitor or a pharmaceutically acceptable salt thereof, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The anti-resistance agents and/or tyrosine kinase inhibitors can be administered by methods well known in the art as described in Donnelly et al. (Ann. Rev. Immunol. 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The anti-resistance agents and/or tyrosine kinase inhibitors can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The anti-resistance agents and/or tyrosine kinase inhibitors can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the anti-resistance agents and/or tyrosine kinase inhibitors are administered intravenously, intraarterially, or intraperitoneally to the subject.

The anti-resistance agents and/or tyrosine kinase inhibitors can be a liquid preparation such as a suspension, syrup, or elixir. The anti-resistance agents and/or tyrosine kinase inhibitors can be incorporated into liposomes, microspheres, or other polymer matrices (such as by a method described in Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The anti-resistance agents and/or tyrosine kinase inhibitors may be used as a vaccine. The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the anti-resistance agents and/or tyrosine kinase inhibitors are administered in a controlled release formulation. The anti-resistance agents and/or tyrosine kinase inhibitors may be released into the circulation, for example. In some embodiments, the anti-resistance agents and/or tyrosine kinase inhibitors may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

7. METHODS a. Methods of Treating Cancer in a Subject

Provided herein are methods of treating cancer in a subject. The methods may include administering to the subject a tyrosine kinase inhibitor and an anti-resistance agent. In some embodiments, the tyrosine kinase inhibitor and the anti-resistance agent are co-administered to the subject. In some embodiments, the tyrosine kinase inhibitor is administered to the subject prior to the anti-resistance agent. In some embodiments, the anti-resistance agent is administered to the subject prior to the tyrosine kinase inhibitor. In some embodiments, the cancer is a tyrosine kinase inhibitor-resistant cancer. In some embodiments, acquired drug resistance to the tyrosine kinase inhibitor is decreased or prevented. In some embodiments, the activity of the tyrosine kinase inhibitor is increased. Inhibition of CYP51A1 or upregulation of miR-764 (SEQ ID NO: 4) can be used as therapeutics for the treatment of lapatinib-resistant lung cancers.

b. Method of Treating Cancer in a Subject Undergoing Treatment with a Tyrosine Kinase Inhibitor Provided herein are methods of treating cancer in a subject undergoing treatment with a tyrosine kinase inhibitor. The methods may include administering to the subject an anti-resistance agent. In some embodiments, the cancer is a tyrosine kinase inhibitor-resistant cancer. In some embodiments, acquired drug resistance to the tyrosine kinase inhibitor is decreased or prevented. In some embodiments, the activity of the tyrosine kinase inhibitor is increased.

c. Method for Preventing Drug Resistance or Enhancing the Therapeutic Efficacy of a Tyrosine Kinase Inhibitor Provided herein are methods for preventing drug resistance or enhancing the therapeutic efficacy of a tyrosine kinase inhibitor in a subject having cancer and undergoing treatment with the tyrosine kinase inhibitor. The methods may include administering to the subject a pharmaceutical composition comprising an anti-resistance agent in an amount effective to attenuate resistance to the tyrosine kinase inhibitor. In some embodiments, acquired drug resistance to the tyrosine kinase inhibitor is decreased or prevented. In some embodiments, the activity of the tyrosine kinase inhibitor is increased.

d. Method of Sensitizing a Tyrosine Kinase Inhibitor-Resistant Cancer

Provided herein are methods of sensitizing a tyrosine kinase inhibitor-resistant cancer in a subject to the tyrosine kinase inhibitor. The methods may include administering to the subject an anti-resistance agent. In some embodiments, acquired drug resistance to the tyrosine kinase inhibitor is decreased or prevented. In some embodiments, the activity of the tyrosine kinase inhibitor is increased. In some embodiments, ketoconazole (a CYP51A1 inhibitor) can be used to sensitize drug resistant cancer cells, and a combination of lapatinib and ketoconazole may be used to prevent acquisition of EGFR-TKI resistance

8. EXAMPLES

Example 1

Polymeric Scaffold

We found that a polymeric nanofibrous scaffold platform allows growth of three-dimensional (3D) tumor-like aggregates (referred to as tumoroids), which resemble in vivo tumors. As detailed in the Examples below, tumoroids exhibited better drug resistance compared to two-dimensional (2D) cultures that lack ability to mimic the environment of the tumor microenvironment. 3D scaffold may be used to elucidate EGFR TKI resistance mechanisms and help design more efficient treatment strategies to block resistance.

Example 2

Establishment of a Multi-Drug Resistant Cell Lines

To investigate drug resistance to EGFR TKIs, we developed lapatinib resistant human lung cancer cell lines as model for de novo drug resistance. To derive drug resistant (DR) cells, H1975 human lung cancer cells, that carry L858R and T790M point mutations in exons 20 and 21 of EGFR, were grown in a static concentration of lapatinib for up to 30 days. We also developed EGFR TKI resistant H1650 and H1299 human lung cancer cell lines to confirm any potential findings in cell lines with different EGFR mutations, thereby enhancing the reproducibility and relevance of the work. The drug sensitivity of the parental and DR cells on both the monolayer and the 3D scaffold were determined by testing a panel of standard-of-care chemotherapeutics along with EGFR TKIs.

Figure 2A:
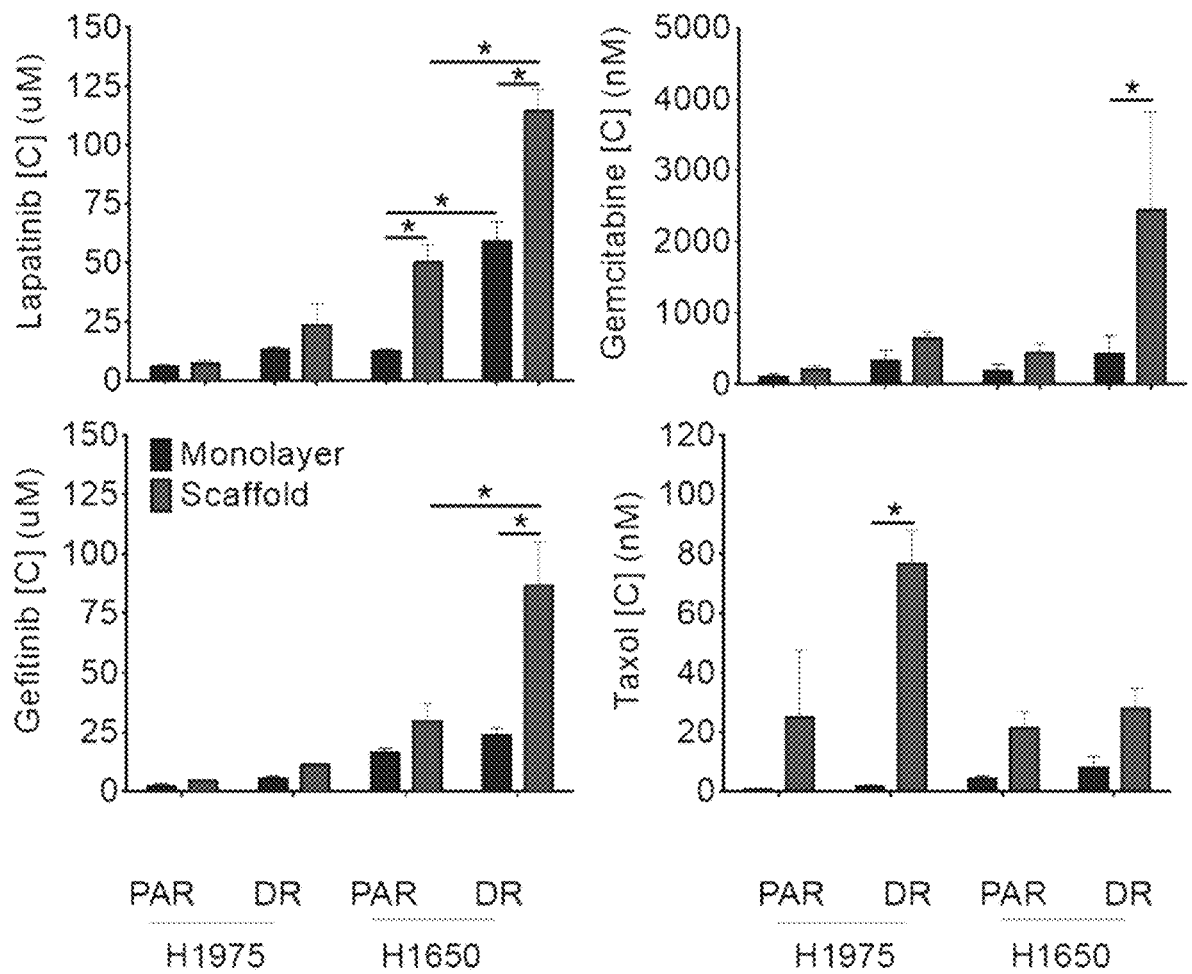
FIG. 2A and FIG. 2B are graphs showing the establishment of multi-drug resistant cell lines. Shown in FIG. 2A is the drug sensitivity in parental- and DR-cell lines. Average luminescence as a percentage of control in lapatinib treated cultures on the monolayer (blue/dark gray) and the scaffold (red/light gray) is shown. Shown in FIG. 2B are images of the H1975 cell line grown on 3D fibrous scaffold (100×).
Figure 2B:
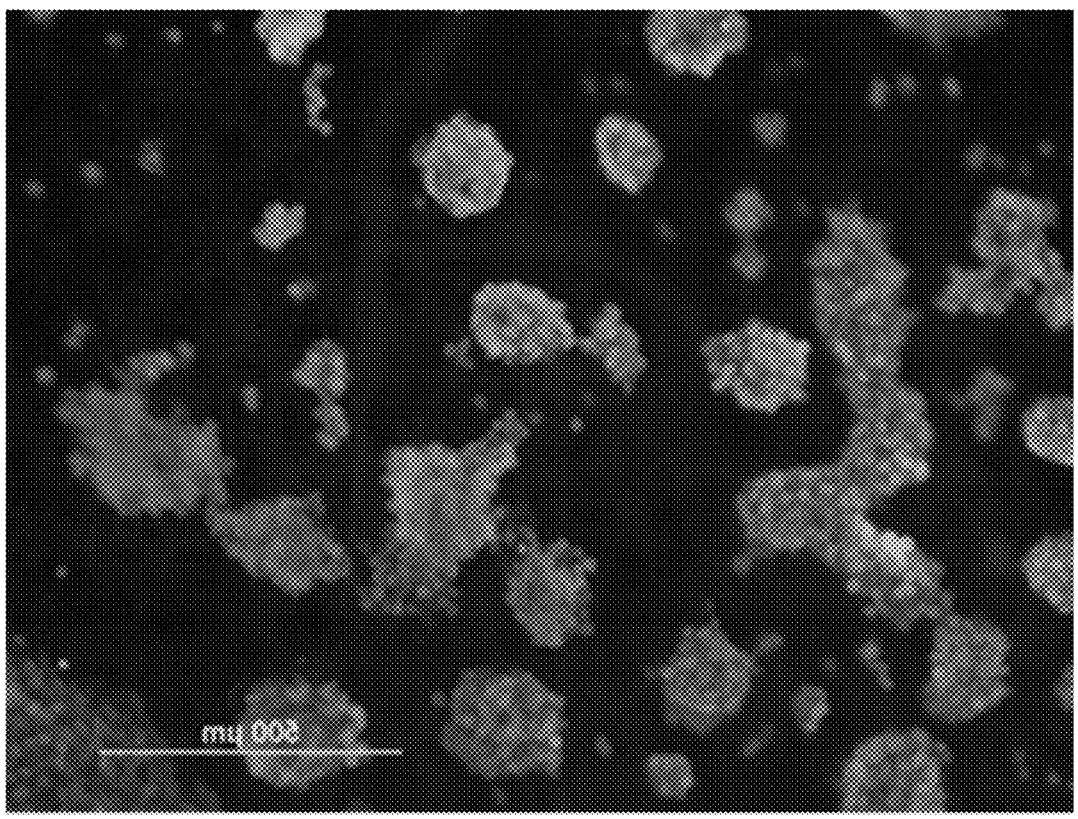
Figure 2B:
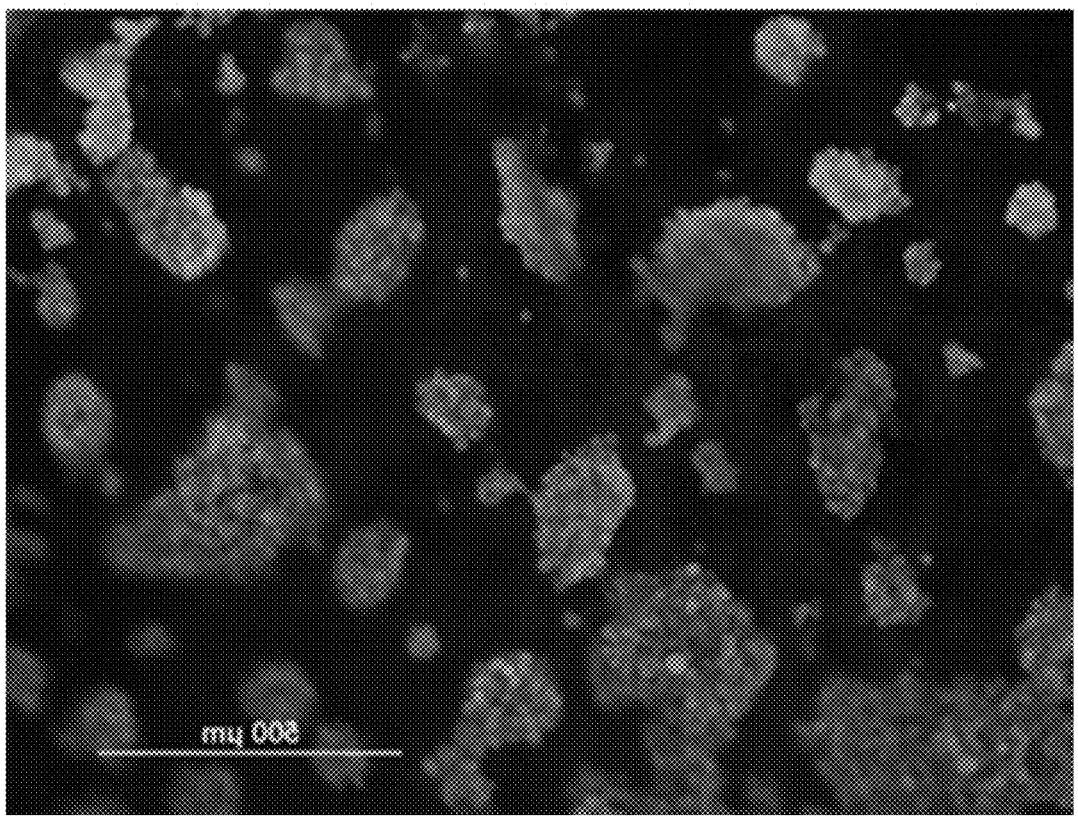

Drug sensitivity in parental- and DR-cell lines were determined. Cells were treated in triplicates with indicated concentrations of the identified drug for 72 hours in monolayer cultures and for 48 hours in scaffold cultures. For cells grown on the scaffold, drugs were added on day 3, as compared to 24 hours for monolayer. Cell viability was determined using Cell Titer Glo assay (Promega). Results are shown in FIG. 2A. Average luminescence as a percentage of control in lapatinib treated cultures on the monolayer (Blue) and the scaffold (Red) is shown. Experiments were repeated at least two times. Graphs and statistical analysis were derived using GraphPad Prism software. Shown in FIG. 2B are images of the H1975 cell line grown on 3D fibrous scaffold (100×).

Example 3

Analysis of Drug-Resistant Versus Parental Cell Lines

To determine the mechanism of resistance, mass spectroscopy was used to determine the relative levels of certain key proteins being expressed in the H1975 and lapatinib DR-H1975 cell lines. The proteomics data collected using mass spec is served as a guide for future experimentation, and all results of intriguing proteins were confirmed and validated in the EGFR TKI resistant models using other methods, including western blotting and mRNA transcript analysis. We also performed a miRNA array to determine relative levels of key miRNAs being expressed in H1975 and lapatinib DR-H1975 cell lines. miRNA transcript analysis was used to validate this data.

A comparison of the drug sensitivity showed that parental cells were at least 3-fold more sensitive to the EGFR TKIs compared to the DR cells. The sensitivity to EGFR TKIs was further decreased when DR cells were cultured on our fibrous 3D scaffold. Furthermore, qPCR analysis showed upregulation of certain cancer stem cell markers, such as OCT-4 and Nanog, when the cells were grown on the 3D scaffold. This may explain the increased resistance seen when the cells are grown on the 3D scaffold. EGFR TKI resistant cells were also resistant to other anti-cancer agents, such as taxol and gemcitabine. Data mining the significantly differentially expressed proteins list generated by the mass spectroscopic analysis revealed that the protein expression is skewed in lapatinib DR-H1975 cell line as compared to the H1975 cell line. Proteins involved in all aspects of homeostasis including metabolism, biosynthesis, and oxidative regulation were significantly up regulated in the lapatinib resistant cell line. The protein CYP51A1, which is directly involved with cholesterol synthesis, was significantly upregulated in the DR-H1975 cells compared to the parental cells. Western blotting confirmed the upregulation of CYP51A1 in lapatinib resistant cell lines. A CYP51A1 inhibitor, ketoconazole, not only inhibited p-EGFR in the H1650-DR cells, but also alleviated development of lapatinib resistant in parental H1650 cells.

The miRNA array revealed down-regulation of miRNA-764 (SEQ ID NO: 4), which miR Walk 2.0 software has predicted will bind to the 3'-UTR of CYP51A1. This may explain the up-regulation of CYP51A1, as binding of miRNA-764 (SEQ ID NO: 4) to the 3'-UTR of CYP51A1 would repress translation of the mRNA.

Figure 3A:
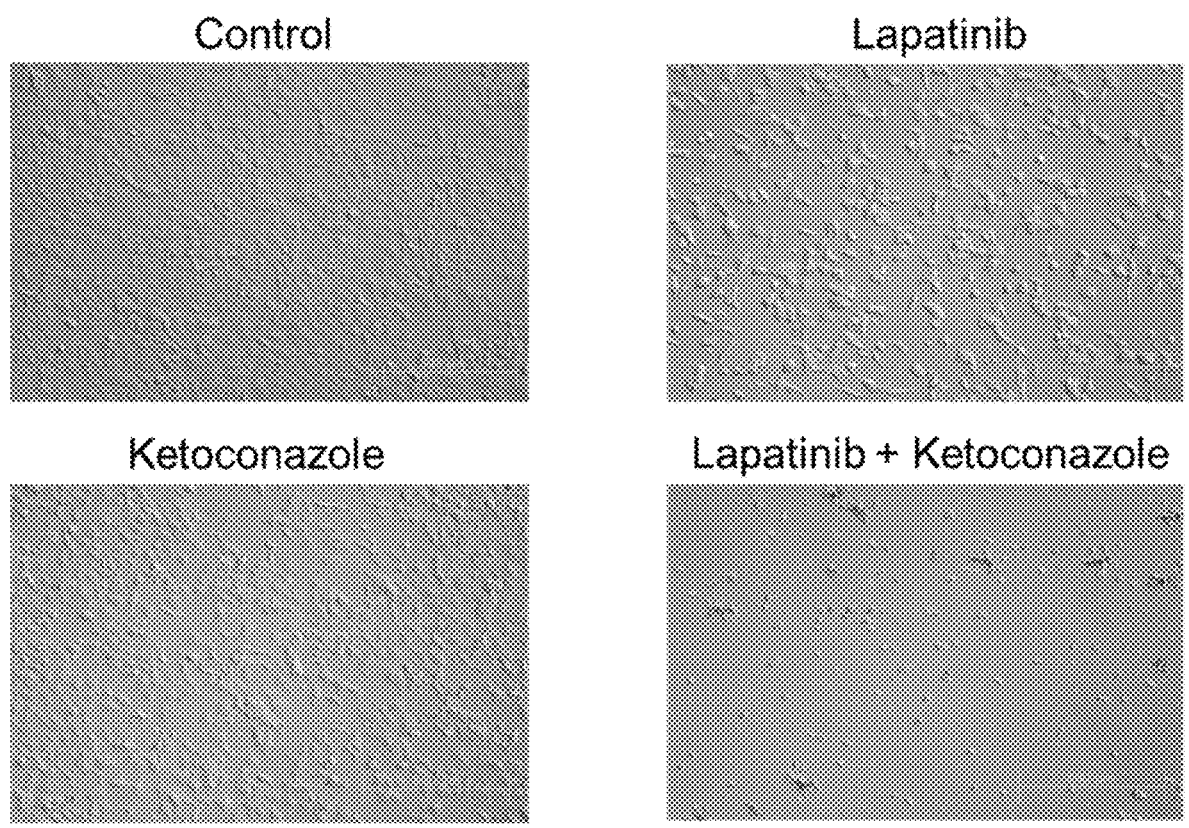

Drug-resistant cells (DR) were compared to parental cell lines. 500,000 H1650 cells were plated in 1 well of a 6-well plate and treated with the indicated drugs at the time of plating. They were allowed to grow for 72 hours. Microscopy pictures were taken using bright field microscopy at 100×, and results are shown in FIG. 3A.

Cells were treated with lapatinib or ketoconazole for 48 hours. The expression of cleaved EGFR, p-EGFR, CYP51A1 were examined using western blotting of the whole cell lysates. β-Actin was included as a loading control. Results are shown in FIG. 3B. Ketoconazole induced lowering of EGFR downstream signaling. Densitometry of western blot bands was performed using ImageJ software, and results are shown in FIG. 3C.

Selected proteins upregulated in lapatinib-resistant H1975 lung cancers cells were compared to the parental cell line. Whole cell lysate for each cell line was run in duplicate. Peptides for each sample were labeled using ITRAQ labeling kit. Data was collected using the Q Exactive Plus mass spectrometer and analyzed first using MaxQuant proteomics software and next uploaded into Scaffold for statistical analysis. Identified proteins were first subjected to a mann-whitney u-test to look for significant differences in protein abundance. Protein abundance was measured by the average intensities between replicates. Proteins that were identified to have a p-value of p≤0.05 were further analyzed to characterize the fold change difference between the groups. Results are shown in TABLE 1.

TABLE 1

Selected proteins upregulated in lapatinib resistant H1975 lung cancers cells compared to the parental cell line.

| Altered Proteins | Fold Change Ratio | T-Test Analysis |
| --- | --- | --- |
| CYP51A1 | 2.01 | 0.021 |
| YWHAH | 1.74 | 0.0032 |
| CPT1A | 1.4 | 0.021 |
| MIC60 | 1.21 | p < 0.0001 |
| MAPK1 | 1.19 | 0.021 |

RNA was then isolated from the cell samples by TRI Reagent® method, quantified by O.D. measurement, and assessed for quality by chip-based capillary electrophoresis on an Agilent 2100 Bioanalyzer RNA 6000 Pico Chip. For each sample, a total of 1,000 nanograms of DNA-free total RNA was used as input into the Affymetrix miRNA FlashTag Biotin HSR RNA Labeling Kit to generate biotin-labeled RNA suitable for hybridization. Approximately 900 nanograms of the biotin-labeled sample was then loaded onto Affymetrix miRNA 4.0 microarrays according to manufacturer protocol. The microarrays were washed and scanned according to manufacturer protocol. Log 2 data for each microarray was exported from the Affymetrix Gene Expression Console and used for statistical analysis. Results are shown in TABLE 2.

TABLE 2

Selected miRNAs differentially regulated in lapatinib resistant H1975 lung cancers cells compared to the parental cell line.

| Altered Proteins | Fold Change Ratio | T-Test Analysis |
| --- | --- | --- |
| miRNA-764 | 1.12 | 0.013 |
| miRNA-3119 | 1.15 | 0.00522 |
| miRNA-330-3p | 0.43 | 0.0193 |

Without being limited to theory, it is possible that upregulation of CYP51A1 in drug resistant cells caused the cell to produce more cholesterol, which is needed for proper membrane and lipid raft formation. This could have caused enhanced EGFR downstream signaling, possibly outcompeting the effects of the inhibitor and leading to resistance.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of treating cancer in a subject, the method comprising administering to the subject a tyrosine kinase inhibitor and an anti-resistance agent.

Clause 2. The method of clause 1, wherein the tyrosine kinase inhibitor and the anti-resistance agent are co-administered to the subject.

Clause 3. The method of clause 1, wherein the tyrosine kinase inhibitor is administered to the subject prior to the anti-resistance agent.

Clause 4. The method of clause 1, wherein the anti-resistance agent is administered to the subject prior to the tyrosine kinase inhibitor.

Clause 5. A method of treating cancer in a subject undergoing treatment with a tyrosine kinase inhibitor, the method comprising administering to the subject an anti-resistance agent.

Clause 6. The method of any one of clauses 1-5, wherein the cancer is a tyrosine kinase inhibitor-resistant cancer.

Clause 7. A method for preventing drug resistance or enhancing the therapeutic efficacy of a tyrosine kinase inhibitor in a subject having cancer and undergoing treatment with the tyrosine kinase inhibitor, the method comprising administering to the subject a pharmaceutical composition comprising an anti-resistance agent in an amount effective to attenuate resistance to the tyrosine kinase inhibitor.

Clause 8. A method of sensitizing a tyrosine kinase inhibitor-resistant cancer in a subject to the tyrosine kinase inhibitor, the method comprising administering to the subject an anti-resistance agent.

Clause 9. The method of any one of clause 1-8, wherein the anti-resistance agent comprises a CYP51A1 inhibitor, or an agonist of SEQ ID NO: 4 (miRNA-764), or a combination thereof.

Clause 10. The method of clause 9, wherein the anti-resistance agent comprises a CYP51A1 inhibitor.

Clause 11. The method of clause 10, wherein the CYP51A1 inhibitor comprises ketoconazole.

Clause 12. The method of clause 9, wherein the anti-resistance agent comprises an agonist of SEQ ID NO: 4 (miRNA-764).

Clause 13. The method of clause 12, wherein the anti-resistance agent comprises a polynucleotide having a sequence of SEQ ID NO: 4 (miRNA-764).

Clause 14. The method of any one of clauses 1-13, wherein the cancer comprises non-small cell lung cancer (NSCLC).

Clause 15. The method of any one of clauses 1-14, wherein acquired drug resistance to the tyrosine kinase inhibitor is decreased or prevented.

Clause 16. The method of clause 15, wherein tyrosine kinase inhibitor resistance is decreased at least 2-fold.

Clause 17. The method of clause 15, wherein tyrosine kinase inhibitor resistance is decreased at least 5-fold.

Clause 18. The method of clause 15, wherein the activity of the tyrosine kinase inhibitor is increased at least 2-fold.

Clause 19. The method of clause 15, wherein the activity of the tyrosine kinase inhibitor is increased at least 5-fold.

Clause 20. The method of any one of clauses 1-19, wherein tyrosine kinase inhibitor comprises lapatinib.

SEQUENCES

SEQ ID NO: 1
CYP51A1 polypeptide (509 amino acids, Accession No. KJ896685)
MAAAAGMLLLGLLQAGGSVLGQAMEKVTGGNLLSMLLIACAFTLSLVYLIRLAAGHLVQLPAGV
KSPPYIFSPIPFLGHAIAFGKSPIEFLENAYEKYGPVFSFTMVGKTFTYLLGSDAAALLFNSKN
EDLNAEDVYSRLTTPVFGKGVAYDVPNPVFLEQKKMLKSGLNIAHFKQHVSIIEKETKEYFESW
GESGEKNVFEALSELIILTASHCLHGKEIRSQLNEKVAQLYADLDGGFSHAAWLLPGWLPLPSF
RRRDRAHREIKDIFYKAIQKRRQSQEKIDDILQTLLDATYKDGRPLTDDEVAGMLIGLLLAGQH
TSSTTSAWMGFFLARDKTLQKKCYLEQKTVCGENLPPLTYDQLKDLNLLDRCIKETLRLRPPVM
IMMRMARTPQTVAGYTIPPGHQVCVSPTVNQRLKDSWVERLDFNPDRYLQDNPASGEKFAYVPF
GAGRHRCIGENFAYVQIKTIWSTMLRLYEFDLIDGYFPTVNYTTMIHTPENPVIRYKRRSK SEQ ID NO: 2
CYP51A1 gene (22378 bp)
```
      1 gtgacgcacg gggtggcgcg cgtgggaccc gaggggtggg gctgggttta gtaggagacc
     61 tggggcaagg cccctgtgg acgaccatct gccagcttct ctcgttccgt cgattgggag
    121 gagcggtggc gacctcggcc ttcagtgttt ccgacggagt gaatggcggc ggcggctggg
    181 atgctgctgc tgggcttgct gcaggcgggt gggtcggtgc tgggccaggc gatggagaag
    241 gtgacaggcg gcaacctctt gtccatgctg ctgatcgcct gcgccttcac cctcagcctg
    301 gtctacctga tccgtctggc cgccggccac ctggtccagc tgcccgcagg ggtggtacgt
    361 acattcttta gggtctgagt ggggcgcgcg ccgcagctga ggcggccgaa gggctggcgt
    421 gggcggctcc gtggcccga ccggctcagt ggatggcaag ggcgggggcg actgcggcca
    481 tgcttggcgt ggctttggtg gcaggcgcgc tgggggctgg agtagtggct gcggcggcgg
    541 cactgctgct ggtggcgctg gctgtagcac ccgccattgc cttgtgttgg ggggcggtgc
    601 tggcctcccc ggctgtgtat ctgatcctag acggggtcgt ggttgcggca tttgtggttg
```

SEQUENCES

```
 661 tagcggtctg tactgaccgc agcagtggtg cccctagtgg cggtggctgg attggcggct
 721 gtgggtttga acgaccggt ggtcgttggg gcccttggtg ggggtcctga cggagatgct
 781 gttggcagct ggcccgtcat cctggaggct gccctgtgtg gttcagtgtt ctgtgggctg
 841 tagcagtgcc cctaatggtg gtttatacc atattaagga ggatgtgtag agtgtggtaa
 901 tggtagtgac tggagtgtgg taagggcctt cctctgatgc taataatgta acagtttctc
 961 ggccgggagc agtggctcac gcctgtaatc ccagcacttc gggaggccga agcgggcgga
1021 tcacctgagg tcaggagttc cagaccagcc tgaacaacat ggagaaaccc catctctact
1081 aaaatacaac aaaacaaaac aaaaattagc tggatgtggt ggcacacgcc tgtagtccca
1141 gctgcttggg aagctgaggc ccgagaatca cttgaaccta ggaggcggag gttgcagtaa
1201 accgagattg cgccactgga ctccagtctg ggcgacagaa tgagactccg tctcaaaaaa
1261 aaaaaaaatc attttcttca atttaacagc cttattaacc tagctttcaa tctcccaaat
1321 gttatttgat tgtgccttt acagtcagca ataagtagct tttgaaaact ccctttac
1381 tgacaatgca atgtacaaac ttttgaccaa gtagcttta aaataatttt tgtttgaacc
1441 ataccaggca taagaaagag ttatttattt atttattttt ttcctcacaca tgggatcttt
1501 aaggaaatga tatttgtctc tgggaagaca aagttacttt tagtgtttaa agatagttct
1561 attagctgag gtgtactgtg aggttgtggt gctccttct atttgagacc accagagaat
1621 tgaggagtat tacccttttt cattattttg tttgattttc aggatactta atgttgtaat
1681 ctgcaggtct cattttgtgg catctaaaga aacttttatg aagaatgcta gagttcttgc
1741 tagagctgat ctactctctt aaaaactcta aaatcagtgg ctctagttca cttgcagtga
1801 gagaagcatg agattgattg tttactgaga agtaaatata gcttcttaaa cattcccctt
1861 ctttctatac tacaagttac tgcttgtctt tttctatacc ttctttaagc aagtatctgg
1921 gactaaaatt gtgagtagta gtagtagtaa gtagtgaaga aacaatatag tgggccctct
1981 ggggacacga attccacatt tgggaattca gccaagtgta gatctaaaat acccagggga
2041 aaaaaaccca atacaaaata acacaacaat aaaaataat acaaataaaa aaacacagtt
2101 taataacagt ttatatagcc tttacattgt attgggtatt gtaagtaata tagaaatggt
2161 ttaaggtata tgagaggatg tgcataggtt atacgcaaat actttgccat tttatataag
2221 ggacttgagg atccctggat acaaatctgt gagggggtcc tgggaccagt tctccacaaa
2281 tgccaaggga caagtgtagt ttgacctttt tggttttttg ctactaatgg ttagaaaagt
2341 tgcctggaga caccaataat aattggacat attctggaca gtgtccatca tttaaattta
2401 cagtgcctta gtgtttatct ggtcgtttat cttataccgt gttttgagtt tctgttcttt
2461 tctacaatag ctactctctt gaggtatttg caatttggct gttctcaagt tacttctgat
2521 gcttcctttt tttttggtaa cttttttttg aagtcttaat agctattttg tttaattgtt
2581 tggtcatgaa acgaaactgg gtttctctct tgaaatgaaa cacgaattga atttactatt
2641 ttttctctt gtagaaaagt cctccataca ttttctcccc aattccattc cttgggcatg
2701 ccatagcatt tgggaaaagt ccaattgaat ttctagaaaa tgcatatgag aaggtaagtc
2761 ttccaaataa ttagaggaaa aaaaaaaaaa caactagaga agtgcttttt aaactttttt
2821 aaaaaagtgg cagaacattt aaaaaccttg taatcatata catatcctca gtataggaaa
2881 caaaatggaa actgctctgg tttaagagat ggtgtcttat agatacctat ccttttagct
2941 tttcccatgt cctggggtcg tctttgagac accattgagg aaacctgtag ttctggcaac
3001 tatggtttaa aagccactgt tctgagtttt ctattcactt attgtcatta aaattgatat
3061 taattaaccc tcattttct ttaccatgca tctgtggggt tttctaacct gctctataca
3121 tcttctgtga tttcactgtc cacttgaatg acccacatga caccatagct actcaattat
3181 ttgcccgtct tctctctaat gagcttccct gtgccagtta agccatttac ttcacagtct
3241 cgctttggac ttgtcactct taactgtttc acttccacaa tattaattta gatatcctat
3301 tcgtagacca taccgtctcc tggtttgctt gtgcaactcc ttaaattata actattcttt
3361 gacctcattg gatcttgcat tccatttact ttctcctgat ccatcagcct tcattcttca
3421 cttcctctt tccgctttgg gtccatggca tgtcgtttct gttacactct tggcaatact
3481 gtactttaaa ttcctcgac cccgcatctt ttcattgtgt tcagctggca gaagtcaccc
3541 ttggaggcag ccagttattg tctccttctg caccagatta gtttcttcct gattttatga
3601 ttgcctacct taatgatatt tgaacactgc tccacagtcc tattatgttc ttgtgattgg
3661 gcctactttt ccactcatta cagtgactaa ttcaaaacctt cactttctta aacttctgaa
3721 tctttctacc tctccatcaa agcagatgat ttttttctcct gtttaggaga caatgattaa
3781 aaacgttgat ttaggagaca attattaaaa cattcaaaga aaacttcctc attttctcaa
3841 tttcaaatat gcaaacctac ttgtatttat atagtaatcc tattctcttt cttcctatca
3901 cagtaataat tatcaaacac ttactttatg ccagtactta gtgcttaca aagatcatct
3961 cactgaagct ccacaaaaac ccttttcaggt atattgttt tatagatgac aaaactgaga
4021 agcagagagg atatataatt tcttcttgga ctcactgcta gacagtggcc aagccaggat
4081 ttacacatgg tctgatttct gagcctatac ttttattaat gataacaata atggaaaaca
4141 agtcattaag atgctaagta agccaaggta ctcttctctg ccctgtatat aaaatttggc
4201 agcagctctg tgaagaactg ctattattat tattaccatt ttataggtga gagaaacgaa
4261 acacagagag actaagttct ctgactatag gaccaaagtc atacagcaag taggtggagg
4321 agctgggatt tgaacacgga cagtctggct cactgcgttc taccacttg attttattac
4381 aactatattt tgcctcttat cggaggctga actctccatc cctcttttgt ctcaggaact
4441 ttttacttt atttgttttc tcagtgtatt gttgacttct ttttcaatgg catctttcct
4501 ttttctctga aaaattcttg tcacccgttt aaaaacttcc tcaaaatggc ttatgaggct
4561 ctgtatggtc tagcactgcc taatgctcaa ctctccattc ctccttttctc tttctcttac
4621 ttttagggcc tttgtgtatg tttagctacc aaaccagctc ctcattcttc tggtctcaac
4681 ctagttgtct tttcctctat taggtctccc tttttttagat tctctcatca cagagttgct
4741 ttcctttctg taatacttgt cacatttgca gttttatgtt tgttaatgtg attatttgat
4801 taatttgtat ttttttccaat agactaagct tggtgagttg ggacagtatt ttttttcatg
4861 attataccccc cagagtctag tcttcaatca taaccagaaa actgcaaggg aaagtattta
4921 acatctaacc aaattaatat aaaataaaaa tgagtagtag ttagtgtagg tgagatagtg
4981 ctaaaataga taaataaact tgtagtgtct tcacatagca ggtactatag aaaaggtcaa
5041 attctttggc tagtcttgta aaatttgttt ttaaccaaag ggggaagaag tctatatttt
5101 cagaggtgtt catcacagaa ttagctgtaa taactaaaga aaaccctgac atatcaccca
5161 tatgtccaat aatgaaagag tagtcagtaa attaacattg tgatgtttat atagacaata
5221 gaaaacattg tcaatataaa ctgaaaaaag cataaataaac agttatattt atactacatt
```

| | | | | | |
|---|---|---|---|---|---|
| 5281 | tgcaactaaa | tgaacataat | tataaatttg | gacaaaggaa | ggaggagtat | ggcaagatga |
| 5341 | aaagaattgc | tttaaggttt | atatatgttt | ttattttttt | aataatgcat | tattttgtga |
| 5401 | ttttaaaaag | ttactgtcgt | agtgttgcat | attttttgta | acatcactat | atgtactttt |
| 5461 | ctcttttag | tatggacctg | tatttagttt | taccatggta | ggcaagacat | ttacttacct |
| 5521 | tctggggagt | gatgctgctg | cactgctttt | taatagtaaa | aatgaagacc | tgaatgcaga |
| 5581 | agatgtctac | agtcgcctga | caacacctgt | gtttgggaag | ggagttgcat | acgatgtgcc |
| 5641 | taatccagta | ggtgacactg | ttaccataaa | taaagacaaa | tctatacctc | agtagttata |
| 5701 | gctaatagtg | agacattata | catttaaaat | gtagaaacag | ccaggcatgg | tggctcattc |
| 5761 | ctgtaatccc | agcactttgg | gaggccaagg | tgggtggatc | actcaaagtc | aggagttcaa |
| 5821 | gaccagcctg | gccaacatgt | gaaaccctg | tctctactaa | aaatacaaaa | attagctggg |
| 5881 | tggggctggt | ggtgcacacc | tgtaaattcc | agctacttgg | gaggctgagg | catgagaatc |
| 5941 | gcttgaaccc | aggaggcgga | ggttgcagtg | agccgagatc | acaacactgc | actttagcct |
| 6001 | tggcaacaga | gtgagaccct | gtctcaaaaa | cagaaacaaa | aaaccaaaca | cacacacaca |
| 6061 | cacgcacgcg | cacacacaca | cacacacaca | cacacacaga | aaccaaccaa | acaaaaatgt |
| 6121 | aataaaatgt | agaaccagtt | tattccttgg | ttcaaaagtc | tgaagaatca | tgagaagaaa |
| 6181 | ggccatggat | aactgataag | taatgggtat | ttagtttat | atttgctgtc | atggctaaac |
| 6241 | aatattaaag | ggcttcctgt | acaaataatg | gaatcaatga | taacttagca | tactgggatt |
| 6301 | taatttgaaa | gggttattag | acaatgctgt | tacttcatca | aaaggacttc | ctgcctaccc |
| 6361 | attcctgcct | gaaattctaa | cataagcgct | gtttagagat | tgctgacttc | agaagtcctc |
| 6421 | ttttaatgca | acaacttcac | gtgtggggta | catctatgtg | tatgttttac | cctcaaaagc |
| 6481 | caaatacgaa | attgttttaa | gttgatatag | aacacaaatc | agacaattgg | ccccaatgct |
| 6541 | tggtatgggc | tctggctgtg | aatgtaacac | acattagcca | gtaccctagt | atagcagtta |
| 6601 | agagttaaca | ttaaatcttg | tttctagtga | tggggaatga | gggaatgaat | gcctctcctt |
| 6661 | aaggccaaaa | aacagggccc | tggaaaatcc | ctctgttcag | atatatatat | tcatttagac |
| 6721 | tctattcatt | tagagtcaga | tagatctatt | catttagact | cttaaaatgt | aaatgcccaa |
| 6781 | agggttaaaa | ccattacttg | tgttagtgtt | acataattat | aataacctaa | atggatttta |
| 6841 | tgataaaaca | aaaatgtgtt | ttaatgccgt | atcccgtttt | tgaattttt | tgaaggtttt |
| 6901 | cttggagcag | aagaaaatgt | taaaaagtgg | ccttaacata | gcccacttta | aacagcatgt |
| 6961 | ttctataatt | gaaaaagaaa | caaaggaata | ctttgagagt | tggggagaaa | gtggagaaaa |
| 7021 | aagtaagcaa | aatgttttat | gtttgtccta | acatttctac | ttctctgtga | atagaaaagt |
| 7081 | agagtatata | tgtgtgtagt | atataaaaaa | caaattacag | tgtatgtaaa | actaccttag |
| 7141 | atttatggga | gggttatgta | atgattacca | tgaagttgta | actgagaatc | cagtttttat |
| 7201 | actgggctgc | aagttaagta | ttgccttcag | aagcaattgc | tgtgcccata | gtaggaagca |
| 7261 | acatctgccc | acagggcagc | aggacccagg | gcagcaggtc | actatattct | gggtctggcc |
| 7321 | tttggcctct | gtaagagttc | cagaatcttt | gttttggta | tacttaagtt | gatattgata |
| 7381 | tattttctaa | ccatacaaga | aactgatgta | taaattagaa | tgccaatgta | ataatgcatg |
| 7441 | tgagacatat | aattacagca | ccaagaaatc | cagaatattt | actgatattc | tttttattga |
| 7501 | caaatataat | tggaaagcca | gatgatcatt | ggaagttcat | ttagtgaatg | tggaattaac |
| 7561 | aggaaattaa | ttggataatt | tttattagtt | gtcatcaaat | tatgcttgcc | tggtgcattt |
| 7621 | gtctccagtg | ttgggatata | ctaattggtg | attatagttt | tcttttacat | atcgccagta |
| 7681 | attccatttt | ggccctgatc | ttcctactt | taacctggga | aataatctga | tctttggcta |
| 7741 | ctattccttg | ggaagtacct | tattattgtc | atatgcacta | taaataacct | tttttctgct |
| 7801 | tttgttattg | tgacctggaa | atcaaataac | cacatttatt | cttttcatga | tgaagtgctc |
| 7861 | atgagtgggg | ttttgagatg | tgtttctggg | atctgttttg | gctgtttaga | gggacagggt |
| 7921 | gcttcacatt | gtttggttta | ttgcccctct | ttgttgttgt | acatagtcac | atgtctgtct |
| 7981 | acagacttt | tttgatgata | tgaataggat | cttgtttctt | cttgagttct | gttttaatt |
| 8041 | ctcaattttc | tttcactttt | tggaaatagt | aatgagaata | atctttttt | tctccctaga |
| 8101 | tgtgtttgaa | gctctttctg | agctcataat | tttaacagct | agccattgtt | tgcatggaaa |
| 8161 | ggaaatcaga | agtcaactca | atgaaaaggt | agcacagctg | tatgcagatt | tggatggagg |
| 8221 | tttcagccat | gcagcctggc | tcttaccagg | ttggctgcct | ttgcctagtt | tcaggtatgg |
| 8281 | ataaagaata | tattacacta | ggttatttaa | ctttgtaaa | ttattgtagt | gttggtatgc |
| 8341 | tttgccttaa | caaagataaa | aattaaacaa | gtaaaacata | caaaatgggt | aagattatga |
| 8401 | atccctttc | ttctataaga | attcaagaca | aattttcttt | atataatgag | ctcattaaa |
| 8461 | gtaagtttca | gtttattaaa | aaggtgattt | gttgtctgtc | tagtctaata | ttttatttat |
| 8521 | gttttgttt | ttgagatgga | gtcttgctct | gttgcccag | ctgtagtgca | gtggtgtgat |
| 8581 | ctcggctcac | tgcagtctct | gcctcctgtg | ttcaagcaat | tctcctgcct | catcctcctg |
| 8641 | agagctggga | ctacaggcac | gtgccaccat | gcccaactaa | tttttctatt | tttagtagag |
| 8701 | acagggtttc | atcatgttgg | ccaggctggt | ttcaaactcc | tgacctcagg | tgatccacct |
| 8761 | gcctcagcct | cccaaagtgt | taggattaca | ggcgtgagcc | actgagccca | gcctagttta |
| 8821 | aaagcctgct | tacctcacgt | attccttatc | ctcaggaaag | tctctgaact | atacctaaaa |
| 8881 | gtgatacagc | tcttctctag | cacttgtttg | aaatctttgg | tggctttta | ttgtattgtg |
| 8941 | aagtttcttt | gttttaaata | tttgtgcctt | tattttaattt | tctgttttct | aaggacaggg |
| 9001 | actgcctctg | atataaagaa | atattgctct | taggacttga | tctatagctt | agtgcttagt |
| 9061 | gttttgcata | ttagtaggct | ttctgtactt | ttgttgattt | attggtgttt | aggtgacaga |
| 9121 | tggggaggag | atagattgct | agtcccttt | cttctatttc | tgccccctct | atctagttac |
| 9181 | agattggaag | aggggtggga | gtaaaaggaa | gagccaggag | agattccta | aagttctctg |
| 9241 | gaactcatca | taccttatat | ttgcaaggag | ctttgcagtt | tcaaaatgtt | ttcatatatc |
| 9301 | ttatattaga | acacccagca | cagccctgga | ctcatagtgg | gttctccata | aatgtgcatt |
| 9361 | tcttttttt | tttttttt | ttggtgatgg | agtcttgctc | tctcgcccag | gctggagtgc |
| 9421 | agtggcatga | gctcggctca | ctgcaagctc | tgcttccag | gttcacgcca | ttctcctgcc |
| 9481 | tcagcctccc | gagtagctgg | gactacaggc | acccgccacc | aagcctggct | aattgttttg |
| 9541 | tactttagt | agagatgggg | tttcaccgtg | ttagccagga | tggtcttgat | ctcccgacct |
| 9601 | tgtgatccgc | ccgcctcggc | ctcccatagt | gctgggatta | caggcgtgag | ccactgcacc |
| 9661 | tggcccataa | atgtacattt | ctacctgcct | gtttctacct | gtctctgtctc | ttggatgaag |
| 9721 | tcagagcttg | ctatgttagg | cccttcacat | tctgcccag | tcttctcttc | ttctactcat |
| 9781 | accaactaat | ttaaccagat | tattcaattc | actttcttaa | acaggctat | gttttcctgg |
| 9841 | ttcgactgta | ttcatacagt | taagccccaa | catcttctct | tctgtacaca | tggtttcagt |

| SEQUENCES |
|---|
| 9901 tgatcctcaa taacagatta acagtcttgt aaatgaaaca gagtaggagt ttttttttaga
9961 aggcttgatt taagaggggg cttgggagtc agactgccta gttttaaatt ccagctccaa
10021 tgtttgcttt ctgtgtgatc ttatgcagct agctataact tgaggttaat agtatgtacc
10081 tcacaggaag ataaaagtga gtaattcatg taaaacactt aacatggtac ctgctacata
10141 gtgaacatac tatttaaagg taaagtttag gagttgaagc ttgtttttctg aatctgctag
10201 tattttcacc ccctacaaaa aactattgta ttagaaagtg aaaagtagaa ccagattcca
10261 tggaagaacc agagtgactc ttctgcttta agacttgatt tggtattaaa attggaattt
10321 tatgttaatt taaaagagta tcctactttc tgttgaactg gaaaatactt ctaaaggaat
10381 ttcttgcttg ttttaggcct ttagtttgaa cacaggcaat gtgttaagaa tctgggatat
10441 atatgttaaa taaagcacag ttcttgccct tagggactat ggacatttt aacaatgtaa
10501 gattttcatg acttccagta tgttcctggt tctgattttt ttgtcaatta ttttagagtc
10561 attaaagttg gttaaataag atgctttatg ctcggtcctg gttctcaaaa tgaatttgat
10621 cctagaaggt tatttctta tttaagaaaa tcatctttat cttttaatta cagacgcagg
10681 gacagagctc atcgggaaat caaggatatt ttctataagg caatccagaa acgcagacag
10741 tctcaagaaa aaattgatga cattctccaa actttactag atgctacata caagtaagag
10801 ctattcagat aacatattaa gctgaagcag gaaattacac attaaaacac agttaaatag
10861 tatttccagt taaaaaacag tgatgctggc aaaataagtt ggtagctgtg atctttggac
10921 tctttaaatt gttgagacat aaactattgg catcctgtgt cttactgtaa tcccagtgac
10981 tgggtatggt aaaagtttgc taatgaactg taatggagtc ttttgtaatc aaaatcgttt
11041 tgtgctggtc tgtctcttcc ctaagagaaa aaaaactctt gacttgtgat agtcaaatat
11101 aagagaccac tatacctgaa aaatgtattc attatgcacac tttatttaaa ggttgaggca
11161 tgaaatgtat ctgccaaaat gttaaatttg tgtctttggt tcattcctta gggatgggcg
11221 tcctttgact gatgatgaag tagcagggat gcttattgga ttactcttgg cagggcagca
11281 tacatcctca actactagtg cttggatggg cttcttttttg gccagagaca aaacacttca
11341 aaaaaaatgt tatttagaac agaaaacagt ctgtggagag aatctgcctc ctttaactta
11401 tgaccaggtt tgttggattt tcagtttca ttgctgcctt atgactttga ggatctgtgg
11461 ctaatttta aaagggacaa tttgagattt tctatatact atagcttaaa ttgatcagct
11521 tctctatttt tagcaaattc cctataacct tacctaaaat atcttaatgt tattgcttct
11581 tgccattaag ctttatcaga tatgtttggg gttgatggct tagagatcct tggggatgtt
11641 tctttggtac ttacttcctc tgcttcaaag tctggcttct gtacatagag gatattatgt
11701 gcatgttgtg tgtcttatga agtgtagaag cctctgaatt acttagaatt ctgtatgtcc
11761 agagtggcct gggcatgagc agagacttct aaaagtagta gtagtagtag taatgaggac
11821 aagacattta caaatactac atgcaacttg ctgggtggaa aggaagagag gacaactcac
11881 tgcacaacct gacattccat cttggaagca aaccttggtg atgtcatctt cctgttatct
11941 tttgtgcttt tggtcctata ttaatatggc acattacact gattttcaga tgttaattgt
12001 attcctggga taaatcctac tttgtcatgg tgcatagttc tttctatatg ttactacata
12061 taaacttgct ggtgtttttgt tgaggatttt tgcatctata ttcataaagg atattgatct
12121 ctagtttcac tgtgatgtct ttgactggtt ttgatatcag gatcatactc atctcataga
12181 atgtatttgg aagtattctt tttttcttct aattttttgga agagtttgtg gatgattggt
12241 gttaatcctt ttttacatat ttgcaaaaat tcagcagtga aatcatctag atctgtgctt
12301 ttcttttctga gaagacttta cttactaatt caatttattt gttacaggtt tattcagata
12361 ttccatttct tcttatgtca gtttcagtag tttatatctc tctaggaatt tgtccatttc
12421 atctaggtta cctaatttgt tggcatacaa ttgttcatag tattctcata atcctttta
12481 ttttctgtaag ctcagtagtg atgtctcaac actcattctt gtttttagta acttaaaata
12541 acagcttaac tgatatattt acatagcata aatccatcca tttaaaatgt acactttgtg
12601 gtttttagca tattaagagt tgggaaacca tcatcataat ttaattttag aacatttaca
12661 tcactcccaa aagagagctg gtacccatta gcagtcatgc ttcattctcc ctgactgctg
12721 cccctggcaa ccattaatct ccttttgcct ctgtgagttt gcctattctg gatatttcat
12781 gtaaatggga tcatacaatt tgtagtcttt tgtgactacc ttgtttcact tagcatgtta
12841 tcagggttct tccatgttgt agcatgtatc agtacttcag tctttgttat taccaataat
12901 attccattat atggatagac cacatttgt ttatttgttc atcagttgat ggacatttga
12961 gttgtttcca cctttaaac tattatgaat aatgccgctc taaacgtttg tgtactgatt
13021 ttatgtggac atgtgttttc aattttgggg ggtcatacct aggagtagaa ttgctgggtt
13081 ataaggtaac tttgaagaac tgccagactg tttaaaaag tggctgcacc actttgcaaat
13141 ctcactaaac agtatatgtt ggtcctgact tcacccctc accaaacttg ttacttgatt
13201 tttttattat aataggtgtg aagtgatact tttttttttt tttttgagac agagtcttgg
13261 tgtgatgccc aggctctagt gcaatggcgc gaccttggct tactgcaacc tcggcttccc
13321 aggttcaagc tattctcctt cctcagcctc ccaagtagct gggtacacac caccacgcct
13381 ggctaatttt tgtatttttg gtagagacaa ggttgtacca tattggccag gctggtcttg
13441 aactcctgac ctcaagtcat ctgcccgcct tggcctccca aagtgctggg attacaggtg
13501 tgagccacca tgcccagttg gtattttgtt ttgatttgc atttccctgg tgactagtga
13561 tgttgagtgt cttatgatgt gttcttttggc tttggtatac ttctttggag aaatgtctgc
13621 tcacatcctg ttcccatatt taaatgagt tgtctttta ttattgagtt gtaagagttc
13681 atctattttt tttaatgtg cttttggtgt cagagaaact aatgcctaat caaagtgtat
13741 gaagatttat ttctgtgtat tcttcttagt gttttgtagt ttcatatctt acatttaggt
13801 ctttgatcca ttatgaatta atttatgtat atgatgtgag gtcatcattc ttttgcatgt
13861 gtttatccag ttgtcccaca ctgtttgttg aaaagactat tttttccacg ttgaattgtc
13921 tttgtaaaaa aatctattat agccaggcgc agtggcacgt gcctgtattc tcagctactg
13981 agaagctgag atgggaaggt cgcttgagct caggacttgg ggtccagcct gggcaacata
14041 gcgaaaccct gtctctgaaa aaataaatac attttaaaaa gcctcttgac cataaattta
14101 aggctttatt tctggactca gttctattcc attgatatgt ttagtctgat gccattacgt
14161 agttttgtaa taagtttgta attcgggagt gtgagtcctc tgacttttgtc ctttcaagg
14221 ctgtttatct actcctagtc cctttagttt ccatatgaat tttgggggtca gtgtgtcagt
14281 ttctgcaaag aagctagctg agattttga caatgattgc attgtatcgc catattaatt
14341 tgggagcaca atttagtctt ttaaatctgt gaacatgaga tgtctttctc ttattttagt
14401 tctttaattt cttttcaacaa tgttttatag ttttttggtgc acaatgttta aacttctctt
14461 gttaaatgta ttcttaagta tttattatt gttattttt tgatgttatt ctttcttctg |

-continued

| SEQUENCES |
|---|

```
14521 ccagtccaaa tctgctgttg atcccctcgg gtgaattttt catttcagtt ctcatacttc
14581 tcagttcttg aatttctatt tggttctcta aaaaaataat atattgatat tctccatttt
14641 actagagata tctaggcata ttttgctata gttctttgaa cctgtttata atagctgatt
14701 taaattcatt atctagtaag tccaatgtct gggcttcttc atggatagtt tctattaaac
14761 tgcttgcttt ttctatgtac tggccatact ttcctgtttt ggtgtgtttt ttgtaatttt
14821 tttgttgaaa actgtacatt taaaataatg tggcaactgt ggaaatcaga tgccctcctc
14881 cctgggttta ttgttgctag ctcttttgttg ttgttgttgt tgctgctgct gtttgtttac
14941 tgcgtttcct ggattaatta tgtcattcct tgttcagtga ggtcactgaa atctctgctt
15001 gcttacttta gtgggcatct aatatttgga cagagattta ctgaagtgct ttgaacagcc
15061 agtctcctag cttttgctga aaggctctgt atgtgtgtgt taggggatgt tattaacact
15121 ccaacaggca gttacaagtc tgccttcact acctgtgtgt acaggtcagc cagaggtaaa
15181 agattacagc ctcttagatc ttacctgggc atatgcatgg tcttatacat atgtgtggcc
15241 ttcaagattc tcttatgttg gaacttttca aagtctcctg tggacatctt actccccagt
15301 tttcccttttt aaacttcttg ttctgtctct tagcaccaac tgatatcacc atctcaggcg
15361 ccttcagtgt taaacaattt ttgctaaata ttttggaaa atttgctctg gctcctctaa
15421 tagttgttag gcttctggct ttcacagctg ctatagttgt catgctgttg gtttccgggg
15481 ctaccatgga tttggggaga ggaggatgaa agaaatacaa cttacactac cacaaagctt
15541 actcttctta ccaagattca gatttctttt tcttgaatta actctcctta gattgttgca
15601 agcctttggt taatcttcca gaattttgaa aaagttgaca ttaagattgt tgctactgtt
15661 ttcattttt ggaggagtga attttttgtag gttcttactt cattcttcag gcaatcgct
15721 tctgttacct tgccctcctt tttcaccatg gacagtggta gagcatgata accccagcca
15781 ccctgaacca gttacctctg tactttttagc tggaatgcaa gctgtcttgt actaactaag
15841 aagttaaact aatttttttgt actgttgaag tatgttattt ataacaatca ggaaatgctt
15901 tctcattttta gctcaaggat ctaaatttac ttgatcgctg tataaaagaa acattaagac
15961 ttagacctcc tataatgatc atgatgagaa tggccagaac tcctcaggtg agtatcttgg
16021 ctacatcttc ccctctatac ccccagtttt tatcaaaaag aagaaatagg tgggtgtggt
16081 ggttcacacc tgtaatctca cactttggg aggctgaggt gggaggatca cttgaggcca
16141 gaatttgaga ccagcctggg caacatagtg agaccgacct catctctaca aaatttttc
16201 taaaaattag ctggccataa tggcacatgc ctgtggtccc agctgcttgg gaggctgatg
16261 tgggtagatt gcttgagcct gggaggttga aactgcagta atccatgatc acgccactgc
16321 attgctgcct gggcaacaga gcaagaccct gtctcaaaaa aaataaaaat aaaaaagaaa
16381 gaaaaagaaa agaggaagta gagtagcata aaagagaatt ttttaaatta aaaaagtaga
16441 ataatcactt ctacctaatc ttcagtttta tatactctaa aaacatattt ttacctaatt
16501 gtagatagta tacgtgctaa tctgtttttt tttttttttga gacggcattt cactcttgtt
16561 gcccaggctg gagtgcagtg gtgcgatctc agctcactgc aacctccgcc tcccgggttc
16621 aagcaattct tctgcctcag cctcccaagt agctgggatt acaggggcat gccaccatgc
16681 ctggctaatt tttttgtattt tagtagagat gggtttttc catgttggtc aggctgatct
16741 cgaactcccg acctcaggtg atccacccgc cttggcctcc caaagtgctg ggattacagg
16801 tgtaatcccg cgccggcct acatgctaat ctttaatgct aatcatgttc tgcattttc
16861 tttaacaatt ggggttttaa aaatcaaagt acatatttt cttggttta aaaataacat
16921 tttgttgtaa aaaattgtta atatgaagta tacaaattga tagtgaaagc ctctctgaaa
16981 ttccaaccct acctccaagg cattatgggt ttgatttgtg tactgtgtac ttccaaccca
17041 acgctggctc actggaaatc atcttgagtt aaaataattt ttagttgcc tattatctag
17101 ccagttttta aatatatgta cagatggttc ttgatttatg tgattcaact tataattttt
17161 tgacttatg atggatttat caggatgtaa acctatcata agtcaaggag catctgagta
17221 tcccatgtat attcatgctt tattacacaa tgatctgatt atttgtcagc acattttaa
17281 attctctaat gaaatgtgtg gcttttgttt atagactgtg gcagggtata ccattcctcc
17341 aggacatcag gtgtgtgttt ctcccactgt caatcaaaga cttaaagact catgggtaga
17401 acgcctggac tttaatcctg atcgctactt acaggataac ccagcatgc gggaaaagtt
17461 tgccatatgtg ccatttggag ctggtaagat gattatattt tagattggaa atgtttgttc
17521 tgataacata tttgtctctg tcaaaatatt ccgaattgtg tttacaaatt atctctccct
17581 ttcctcatag ggacatttt gcaaacttt ttaggagaag aatctttata agttggagaa
17641 aaatattttcc tttgtaccaa atggaattgt tccataaatc cttatataat gcttcactac
17701 ttcctaacct gtctggtttt attaggtcta atttttatag aacatccttg ttttcccttta
17761 caatggtatt taaagctctt tgtggattct cttttaaaga accattggag tcagcacacc
17821 attcagggaa taacagatta ctagcatttc acaaaaaagc aaaggcagtc ttttaaaatt
17881 aaagctcttc tcgatcgtta gtcaacattt ttgctctcta aatatccgta tgagaaaatg
17941 gtctttaaat ttgggcaggt tgtgtgtagg cttgcaaatt tcatttccag taagatccta
18001 aaataattta gctataccct tgtttctcca gtaatttctc tgtccattgg ttctctgtac
18061 tgattaaact atattctatg ctttagtctt tccaaggga tcatttaaat gacagatgac
18121 ttgtcattgg tcacactttt tccacatata aaggaaaata taaagtccctt tgggaacttc
18181 agatcttaac tttatgtaat aaatttaata ctgtggtgta taacacaata tataaaagaa
18241 tcatagtttt ttttttgaga gagtcttgct ctgtcaccca gtctggagtg cagtggcaca
18301 atctctcagc tcactgcaac ctccacctct gggttcaagt aattctcgtg ccttagcctc
18361 ctgagtagct gggattacag gtgtgtacca ccacgctcag ctaattttg agcttttagt
18421 agagactggg ttttgccatg ttggccaggc tggtctgaa ttccaggctt gaagcaatct
18481 gcccaccttg gcctcccaca gtgctgggat tacaggcgtg agccatgcca cctggccaaa
18541 gaatcagatt gttaacagat gggaagagca ttagttctgt agcccaaatt ctgccccaaa
18601 gaggaatcgt ttctaaacta gtaattatct ggtttccact tgaactttac tagaaatggg
18661 ttgtggggtg ttcagttacc ttttatgatg gctcattcta tgtttggaca gctgtcattt
18721 ttagagcctt atgttaaagc tgaaatctgt ttctttttaa catctcattt atagttggtc
18781 ctaacccatag tctctgaact tatattgtat gaggtatttg agtacagata taatgtctcc
18841 tccatctttt tttcaatctt tgtgttagtt tcctagggct tctgtaacta attacaatat
18901 gggtggctta aaacaataga aatatattct atcacagttt tggaggctgg aagtgtgaaa
18961 tcaaggtatt ggcaggaccg tgctcctcct taaggttcta caggagaatc cttccttgca
19021 tcttcctagc ttctggtggc tcttggcaac ccttggcttg taactacatt gttccaatta
19081 ctaccctgt cttcaacagg ctttcttctt gttcatgtct ctgtatctta acatggcatt
```

-continued

```
               SEQUENCES 19141 cttataagga caccagtcat tggatctaag tcctaccta  agtcagggtc atctcatctt
19201 aaataattgt gtatataaag atcctatttc ccaattaaga tcacattcta aggttctgga
19261 tggacttgaa tttatggggg gatatatgat cttacgttaa tcttgttaaa tatcacatta
19321 catgtctcta atttctttac tcattctttt acctcgtaat tgtgctgttt atttatgttg
19381 gtgcatatag ttcattcatt ttcataatat tacattttgt gaatcatcag aatttatcta
19441 ctcttatgtt gattcaatta ggatacttct tgcttgttgc gattaaatcc ttggactatt
19501 cttcctgtaa gccaagcttc tcttagttg  ttatatttga aatatggacc aatttgtaaa
19561 tgctcatctt aaatgtcact cctagaaata agtacagtta tgggccaagc aagcactgtg
19621 ctaagcacta tcagtttagg ttttttcttt tgatgaaaaa tcttgcaatg aaatgcccaa
19681 atcttaagtc aacattcatt gagttttgac aaatgaataa cctttagttt agtccaatgt
19741 atcaatcttt taaatggtta ttgcttctg  gccctgtctt aaaattttg  cttagccct
19801 gagtcatgaa gatattctcc tgttcttctc tactgaaatt tatgctgtta gcatcatggt
19861 ttgtgaccct tcttgaatta gtatttgatt atggtgtgac ataggagttg aatttcattt
19921 ttcccccatg taatatctag ttattcctgg accttatgtt gaaaagactt gcttttcctc
19981 attggcttgc tttggtgtct gtactgataa tcaaataacc ataaaaatat tctgttctgg
20041 gctctctgct ctgttccatt gatctatttg ttgatcctta cctagtacca ctctgtttta
20101 tctttagtct tgaagtcaga tttgaaatca gttttatgtc ctccaactca gttctttttc
20161 caagattgct ttggatatcc taggtccttt gcattttat  atgcatttta gaatcagctt
20221 gtcagtttct acatgggtgt gactttttag tatattttt  tgggttcatt aaatctcatt
20281 ttcttccata catttataat gacatttgag gtttgattgg aaggtttca  tattgacttt
20341 taactagggc tttcttggga caaacagaat attctactat attcccaaac tagattacca
20401 tcttatgatt caaacttttcc atatatttaa cccagatata tattttcaga aaaagtaatt
20461 ggaaaagtta tgtgatcagt caagtactgt tttcctaaaa tgtggtattg aaaatctcct
20521 ggaattttta ataattcatg ttgttttatg tgaaaagaat gtcatctttt tattatatta
20581 tctgtacatt tgctgttcat ctaaaatgta gataatatca ccccaggcta aaaaggatga
20641 gaaagaattt aaactgattc ttataacttt ttcttttttt tagggcgtca tcgttgtatt
20701 ggggaaaatt ttgcctatgt tcaaattaag acaatttggt ccactatgct tcgtttatat
20761 gaatttgatc tcattgatgg atacttttccc actgtgaatt atacaactat gattcacacc
20821 cctgaaaacc cagttatccg ttacaaacga agatcaaaat gaaaaaggtt gcaaggaacg
20881 aatatatgtg attatcactg taagccacaa aggcattcga agagaatgaa gtgtacaaaa
20941 caactcttgt agtttactgt tttttaagt  gtgtaattct aaaagccagt ttatgattta
21001 ggattttgtt aactgaatgg ttctatcaaa tataatagca tttgaaacat tttctaatag
21061 ttatgatact tatacatgtg ctttcaggaa gttccttggt gaaacaattg ttgagggggg
21121 atctaggtaa ttggcagatt ctaaataata taatttccag atagtaattt taagagtact
21181 catcgctctt gccaaataag ttcagggtat tcaaatcttg gactagtcct gcaaggtata
21241 aagaataaaa atcccagtga gatacttgga aaccacagtt tattattatt tatctgggca
21301 attattgtgt gtgtgaggat ggaaggggtag ggaataaatcg aacatctaaa gccttgaata
21361 agagaatact aattgttttg gtatgatgat actcagaaat ggagatatta taggaaaaag
21421 aaatcctttg gaattttaac taaaatcact gcatatggga aattaagaga tccaggacca
21481 tatttgataa gagttcctaa aaataatgta attattaatg ctaaagactg ctcatgtatc
21541 ttgatctaat tactaaataa ttacatattt atttacctga taaatatgta tctagttcta
21601 caaggtcaca tttatgtgga agtccaaagt caagtcctta ggggataatt ttgttttggc
21661 tcagttgttc cctgcttcct ttttttttt   tttttttga  gatggagtct cgctctgttg
21721 cccaggctgg agtgcagtgg tgcgatctca gctcactgca tcctctgcct cccgggttca
21781 agcaattctc tgcctcagcc tcccaagtag ttgggattac aggcacctgc caccatgcct
21841 ggctaatttt ttgtattttt agtagagacg gggggtttcac tatgttggcc aggctggtct
21901 tgaactcctg acctcgtgat ccaccgcct   tggcctccca aagtgctggg attacaggca
21961 tgagccaccg cacctggcct tccctgcttc ctctctagaa tccaattagg gatgtttgtt
22021 actactcata ttgattaaaa cagttaacaa acttttttct ttttaaaatg tgagatcagt
22081 gaactctggt tttaagataa tctgaaacaa ggtccttggg agtaataaaa ttggtcacat
22141 tctgtaaagc acattctgtt taggaatcaa cttatcttcaa attgtaactc ggggcctaac
22201 tatatgagat ggctgaaaaa ataccacatc gtctgttttc actaggtgat gccaaaatat
22261 tttgctttat gtatattaca gttcttttta aaacactgga agactcatgt taaactctaa
22321 ttgtgaaggc agaatctctg ctaattttc  agattaaaat tctctttgaa aaaataca
```

SEQ ID NO: 3
CYP51A1 mRNA (1659 nt, Accession No. KJ896685)

```
    1 gttcgttgca acaaattgat gagcaatgct ttttataat  gccaactttg tacaaaaaag
   61 ttggcatggc ggcggcggct gggatgctgc tgctgggctt gctgcaggcg ggtgggtcgg
  121 tgctgggcca ggcgatggag aaggtgacag gcggcaacct cttgtccatg ctgctgatcg
  181 cctgcgcctt caccctcagc ctggtctacc tgatccgtct ggccgccggc cacctggtcc
  241 agctgcccgc aggggtgaaa agtcctccat acattttctc cccaattcca ttccttggc
  301 atgccatagc atttgggaaa agtccaattg aatttctaga aaatgcatat gagaagtatg
  361 gacctgtatt tagttttacc atggtaggca agacatttac ttaccttctg gggagtgatg
  421 ctgctgcact gcttttaat  agtaaaaatg aagacctgaa tgcagaagat gtctacagtc
  481 gcctgacaac acctgtgttt gggaagggag ttgcatacga tgtgcctaat ccagttttct
  541 tggagcagaa gaaaatgtta aaaagtggcc ttaacatagc ccactttaaa cagcatgttt
  601 ctataattga aaaagaaaca aaggaatact tgagagttg  gggagaaagt ggagaaaaaa
  661 atgtgtttga agctcttttct gagctcataa ttttaacagc tagccattgt ttgcatggaa
  721 aggaaatcag aagtcaactc aatgaaaagg tagcacagct gtatgcagat ttggatggag
  781 gtttcagcca tgcagcctgg ctcttaccag gttggctgcc tttgcctagt ttcagacgca
  841 gggacagagc tcatcgggaa atcaaggata tttctataaa ggcaatcgaa aaacgcagac
  901 agtctcaaga aaaaattgat gacattctcc aaactttact agatgctaca tacaaggatg
  961 ggcgtccttt gactgatgat gaagtagcag ggatgcttat tggattactc ttggcagggc
 1021 agcatacatc ctcaactact agtgcttgga tgggcttctt tttggccaga gacaaaacac
 1081 ttcaaaaaaa atgttattta gaacagaaaa cagtctgtgg agagaatctg cctcctttaa
 1141 cttatgacca gctcaaggat ctaaatttac ttgatcgctg tataaaagaa acattaagac
```

-continued

| SEQUENCES |
|---|
| 1201 ttagacctcc tgtaatgatc atgatgagaa tggccagaac tcctcagact gtggcagggt
1261 ataccattcc tccaggacat caggtgtgtg tttctcccac tgtcaatcaa agacttaaag
1321 actcatgggt agaacgcctg gactttaatc ctgatcgcta cttacaggat aacccagcat
1381 caggggaaaa gtttgcctat gtgccatttg gagctgggcg tcatcgttgt attggggaaa
1441 attttgccta tgttcaaatt aagacaattt ggtccactat gcttcgttta tatgaatttg
1501 atctcattga tggatacttt cccactgtga attatacaac tatgattcac acccctgaaa
1561 acccagttat ccgttacaaa cgaagatcaa aatgcccaac tttcttgtac aaagttggca
1621 ttataagaaa gcattgctta tcaatttgtt gcaacgaac |

SEQ ID NO: 4
miRNA-764 MI0003944
aaucuaggaggcaggugcucacuuguccuccuccaugcuuggaaaaugcagggaggaggccaua
guggcaacuguuaccaugauu

---

The invention claimed is:

1. A method of treating cancer in a subject, the method comprising administering to the subject a tyrosine kinase inhibitor and an anti-resistance agent, wherein the anti-resistance agent comprises a CYP51A1 inhibitor, or an agonist of SEQ ID NO: 4 (miRNA-764), or a combination thereof, and wherein the cancer is a tyrosine kinase inhibitor-resistant cancer.

2. The method of claim 1, wherein the tyrosine kinase inhibitor and the anti-resistance agent are co-administered to the subject.

3. The method of claim 1, wherein the tyrosine kinase inhibitor is administered to the subject prior to the anti-resistance agent.

4. The method of claim 1, wherein the anti-resistance agent is administered to the subject prior to the tyrosine kinase inhibitor.

5. A method of treating cancer in a subject undergoing treatment with a tyrosine kinase inhibitor, the method comprising administering to the subject an anti-resistance agent, wherein the anti-resistance agent comprises a CYP51A1 inhibitor, or an agonist of SEQ ID NO: 4 (miRNA-764), or a combination thereof, and wherein the cancer is a tyrosine kinase inhibitor-resistant cancer.

6. The method of claim 1, wherein the cancer comprises non-small cell lung cancer (NSCLC).

7. The method of claim 1, wherein acquired drug resistance to the tyrosine kinase inhibitor is decreased or prevented.

8. The method of claim 7, wherein tyrosine kinase inhibitor resistance is decreased at least 2-fold.

9. The method of claim 7, wherein tyrosine kinase inhibitor resistance is decreased at least 5-fold.

10. The method of claim 7, wherein the activity of the tyrosine kinase inhibitor is increased at least 2-fold.

11. The method of claim 7, wherein the activity of the tyrosine kinase inhibitor is increased at least 5-fold.

12. The method of claim 1, wherein the tyrosine kinase inhibitor comprises lapatinib.

* * * * *

SEQUENCE LISTING

<160> NUMBER OF SEQ ID NOS: 4

<210> SEQ ID NO 1
<211> LENGTH: 509
<212> TYPE: PRT
<213> ORGANISM: Homo sapiens

<400> SEQUENCE: 1

Met Ala Ala Ala Ala Gly Met Leu Leu Leu Gly Leu Leu Gln Ala Gly
1               5                   10                  15

Gly Ser Val Leu Gly Gln Ala Met Glu Lys Val Thr Gly Gly Asn Leu
            20                  25                  30

Leu Ser Met Leu Leu Ile Ala Cys Ala Phe Thr Leu Ser Leu Val Tyr
        35                  40                  45

Leu Ile Arg Leu Ala Ala Gly His Leu Val Gln Leu Pro Ala Gly Val
    50                  55                  60

Lys Ser Pro Pro Tyr Ile Phe Ser Pro Ile Pro Phe Leu Gly His Ala
65                  70                  75                  80

Ile Ala Phe Gly Lys Ser Pro Ile Glu Phe Leu Glu Asn Ala Tyr Glu
                85                  90                  95

Lys Tyr Gly Pro Val Phe Ser Phe Thr Met Val Gly Lys Thr Phe Thr
            100                 105                 110

Tyr Leu Leu Gly Ser Asp Ala Ala Ala Leu Leu Phe Asn Ser Lys Asn
        115                 120                 125

Glu Asp Leu Asn Ala Glu Asp Val Tyr Ser Arg Leu Thr Thr Pro Val
    130                 135                 140

Phe Gly Lys Gly Val Ala Tyr Asp Val Pro Asn Pro Val Phe Leu Glu
145                 150                 155                 160

Gln Lys Lys Met Leu Lys Ser Gly Leu Asn Ile Ala His Phe Lys Gln
                165                 170                 175

His Val Ser Ile Ile Glu Lys Glu Thr Lys Glu Tyr Phe Glu Ser Trp
            180                 185                 190

Gly Glu Ser Gly Glu Lys Asn Val Phe Glu Ala Leu Ser Glu Leu Ile
        195                 200                 205

Ile Leu Thr Ala Ser His Cys Leu His Gly Lys Glu Ile Arg Ser Gln
    210                 215                 220

Leu Asn Glu Lys Val Ala Gln Leu Tyr Ala Asp Leu Asp Gly Gly Phe
225                 230                 235                 240

Ser His Ala Ala Trp Leu Leu Pro Gly Trp Leu Pro Leu Pro Ser Phe
                245                 250                 255

```
Arg Arg Arg Asp Arg Ala His Arg Glu Ile Lys Asp Ile Phe Tyr Lys
            260                 265                 270
Ala Ile Gln Lys Arg Arg Gln Ser Gln Glu Lys Ile Asp Asp Ile Leu
        275                 280                 285
Gln Thr Leu Leu Asp Ala Thr Tyr Lys Asp Gly Arg Pro Leu Thr Asp
    290                 295                 300
Asp Glu Val Ala Gly Met Leu Ile Gly Leu Leu Leu Ala Gly Gln His
305                 310                 315                 320
Thr Ser Ser Thr Thr Ser Ala Trp Met Gly Phe Phe Leu Ala Arg Asp
                325                 330                 335
Lys Thr Leu Gln Lys Lys Cys Tyr Leu Glu Gln Lys Thr Val Cys Gly
            340                 345                 350
Glu Asn Leu Pro Pro Leu Thr Tyr Asp Gln Leu Lys Asp Leu Asn Leu
        355                 360                 365
Leu Asp Arg Cys Ile Lys Glu Thr Leu Arg Leu Arg Pro Pro Val Met
    370                 375                 380
Ile Met Met Arg Met Ala Arg Thr Pro Gln Thr Val Ala Gly Tyr Thr
385                 390                 395                 400
Ile Pro Pro Gly His Gln Val Cys Val Ser Pro Thr Val Asn Gln Arg
                405                 410                 415
Leu Lys Asp Ser Trp Val Glu Arg Leu Asp Phe Asn Pro Asp Arg Tyr
            420                 425                 430
Leu Gln Asp Asn Pro Ala Ser Gly Glu Lys Phe Ala Tyr Val Pro Phe
        435                 440                 445
Gly Ala Gly Arg His Arg Cys Ile Gly Glu Asn Phe Ala Tyr Val Gln
    450                 455                 460
Ile Lys Thr Ile Trp Ser Thr Met Leu Arg Leu Tyr Glu Phe Asp Leu
465                 470                 475                 480
Ile Asp Gly Tyr Phe Pro Thr Val Asn Tyr Thr Thr Met Ile His Thr
                485                 490                 495
Pro Glu Asn Pro Val Ile Arg Tyr Lys Arg Arg Ser Lys
            500                 505

<210> SEQ ID NO 2
<211> LENGTH: 22378
<212> TYPE: DNA
<213> ORGANISM: Homo sapiens

<400> SEQUENCE: 2
gtgacgcacg gggtggcgcg cgtgggaccc gaggggtggg gctgggttta gtaggagacc    60
tggggcaagg cccccctgtgg acgaccatct gccagcttct ctcgttccgt cgattgggag   120
gagcggtggc gacctcggcc ttcagtgttt ccgacggagt gaatggcggc ggcggctggg   180
atgctgctgc tgggcttgct gcaggcgggt gggtcggtgc tgggccaggc gatggagaag   240
gtgacaggcg gcaacctctt gtccatgctg ctgatcgcct cgccttcac cctcagcctg   300 gtctacctga tccgtctggc cgccggccac ctggtccagc tgcccgcagg ggtggtacgt   360
acattcttta gggtctgagt ggggcgcgcg ccgcagctga gcggccgaa gggctggcgt   420 gggcggctcc gtggccccga ccggctcagt ggatggcaag gcgggggcg actgcggcca   480 tgcttggcgt ggctttggtg gcaggcgcgc tgggggctgg agtagtggct gcggcggcgg   540
cactgctgct ggtggcgctg gctgtagcac ccgccattgc cttgtgttgg ggggcggtgc   600
tggcctcccc ggctgtgtat ctgatcctag acggggtcgt ggttgcggca tttgtggttg   660
tagcggtctg tactgaccgc agcagtggtg cccctagtgg cggtggctgg attggcggct   720
```

```
gtgggtttga acgacccggt ggtcgttggg gcccttggtg ggggtcctga cggagatgct    780
gttggcagct ggcccgtcat cctggaggct gccctgtgtg gttcagtgtt ctgtgggctg    840
tagcagtgcc cctaatggtg gtttataccc atattaagga ggatgtgtag agtgtggtaa    900
tggtagtgac tggagtgtgg taagggcctt cctctgatgc taataatgta acagtttctc    960
ggccgggagc agtggctcac gcctgtaatc ccagcacttc gggaggccga agcgggcgga   1020
tcacctgagg tcaggagttc agaccagcc tgaacaacat ggagaaaccc catctctact    1080
aaaatacaac aaaacaaaac aaaaattagc tggatgtggt ggcacacgcc tgtagtccca   1140
gctgcttggg aagctgaggc ccgagaatca cttgaaccta ggaggcggag gttgcagtaa   1200
accgagattg cgccactgga ctccagtctg ggcgacagaa tgagactccg tctcaaaaaa   1260
aaaaaaaatc attttcttca atttaacagc cttattaacc tagctttcaa tctcccaaat   1320
gttatttgat tgtgcctttt acagtcagca ataagtagct tttgaaaact ccccttttac   1380
tgacaatgca atgtacaaac ttttgaccaa gtagctttta aataattttt tgtttgaacc   1440
ataccaggca taagaaagag ttatttattt atttattttt ttcctacaca tgggatcttt   1500
aaggaaatga tatttgtctc tgggaagaca aagttacttt tagtgtttaa agatagttct   1560
attagctgag gtgtactgtg aggttgtggt gctccttct atttgagacc accagagaat    1620
tgaggagtat tacccttttt cattattttg tttgatttc aggatactta atgttgtaat    1680
ctgcaggtct cattttgtgg catctaaaga aacttttatg aagaatgcta gagttcttgc   1740
tagagctgat ctactctctt aaaaactcta aaatcagtgg ctctagttca cttgcagtga   1800
gagaagcatg agattgattg tttactgaga agtaaatata gcttcttaaa catttccctt   1860
ctttctatac tacaagttac tgcttgtctt tttctatacc ttctttaagc aagtatctgg   1920
gactaaaatt gtgagtagta gtagtagtaa gtagtgaaga aacaatatag tgggccctct   1980
ggggacacga attccacatt tgggaattca gccaagtgta gatctaaaat acccagggga   2040
aaaaaaccca atacaaaata acacaacaat aaaaaataat acaaataaaa aaacacagtt   2100
taataacagt ttatatagcc tttacattgt attgggtatt gtaagtaata tagaaatggt   2160
ttaaggtata tgagaggatg tgcataggtt atacgcaaat actttgccat tttatataag   2220
ggacttgagg atccctggat acaaatctgt gaggggtcc tgggaccagt tctccacaaa    2280
tgccaaggga caagtgtagt ttgacctttt tggttttttg ctactaatgg ttagaaaagt   2340
tgcctggaga caccaataat aattggacat attctggaca gtgtccatca tttaaattta   2400
cagtgcctta gtgtttatct ggtcgttat cttataccgt gttttgagtt tctgttcttt    2460
tctacaatag ctactctctt gaggtatttg caatttggct gttctcaagt tacttctgat   2520
gcttcctttt tttttggtaa ctttttttg aagtcttaat agctatttg tttaattgtt    2580 tggtcatgaa acgaaactgg gtttctctct tgaaatgaaa cacgaattga atttactatt   2640 ttttctctt gtagaaaagt cctccataca ttttctcccc aattccattc cttgggcatg    2700
ccatagcatt tgggaaaagt ccaattgaat ttctagaaaa tgcatatgag aaggtaagtc   2760
ttccaaataa ttagaggaaa aaaaaaaaaa caactagaga agtgcttttt aaactttttt   2820
aaaaaagtgg cagaacattt aaaaacattg taatcatata catatcctca gtataggaaa   2880
caaaatggaa actgctctgg tttaagagat ggtgtcttat agatacctat ccttttagct   2940
tttcccatgt cctggggtcg tctttgagac accattgagg aaacctgtag ttctggcaac   3000
tatggtttaa aagccactgt tctgagtttt ctattcactt attgtcatta aaattgatat   3060
```

```
taattaaccc tcattttct ttaccatgca tctgtggggt tttctaacct gctctataca    3120
tcttctgtga tttcactgtc cacttgaatg acccacatga caccatagct actcaattat    3180
ttgcccgtct tctctctaat gagcttccct gtgccagtta agccatttac ttcacagtct    3240
cgctttggac ttgtcactct taactgtttc acttccacaa tattaattta gatatcctat    3300
tcgtagacca taccgtctcc tggtttgctt gtgcaactcc ttaaattata actattcttt    3360
gacctcattg gatcttgcat tccatttact ttctcctgat ccatcagcct tcattcttca    3420
ctttcctctt tccgctttgg gtccatggca tgtcgtttct gttacactct tggcaatact    3480
gtactttaaa tttcctcgac cccgcatctt ttcattgtgt tcagctggca gaagtcaccc    3540
ttggaggcag ccagttattg tctccttctg caccagatta gtttcttcct gattttatga    3600
ttgcctacct taatgatatt tgaacactgc tccacagtcc tattatgttc ttgtgattgg    3660
gcctactttt ccactcatta cagtgactaa ttcaaaccct cacttttcta aacttctgaa    3720
tctttctacc tctccatcaa agcagatgat ttttctcct gtttaggaga caatgattaa     3780
aaacgttgat ttaggagaca attattaaaa cattcaaaga aaacttcctc attttctcaa    3840
tttcaaatat gcaaacctac ttgtatttat atagtaatcc tattctcttt cttcctatca    3900
cagtaataat tatcaaacac ttactttatg ccagtactta gtgctttaca aagatcatct    3960
cactgaagct ccacaaaaac cctttcaggt atatttgttt tatagatgac aaaactgaga    4020
agcagagagg atatataatt tcttcttgga ctcactgcta gacagtggcc aagccaggat    4080
ttacacatgg tctgatttct gagcctatac ttttattaat gataacaata atggaaaaca    4140
agtcattaag atgctaagta agccaaggta ctcttctctg ccctgtatat aaaatttggc    4200
agcagctctg tgaagaactg ctattattat tattaccatt ttataggtga gagaaacgaa    4260
acacagagag actaagttct ctgactatag gaccaaagtc atacagcaag taggtggagg    4320
agctgggatt tgaacacgga cagtctggct cactgcgttc taccactttg attttattac    4380
aactatattt tgcctcttat cggaggctga actctccatc cctcttttgt ctcaggaact    4440
ttttactttt atttgttttc tcagtgtatt gttgacttct ttttcaatgg catctttcct    4500
ttttctctga aaaattcttg tcacccgttt aaaaacttcc tcaaaatggc ttatgaggct    4560
ctgtatggtc tagcactgcc taatgctcaa ctctcatctc ctcctttctc tttctcttac    4620
ttttagggcc tttgtgtatg tttagctacc aaaccagctc ctcattcttc tggtctcaac    4680
ctagttgtct tttcctctat taggtctccc ttttttagat tctctcatca cagagttgct    4740
ttcctttctg taatacttgt cacatttgca gttttatgtt tgttaatgtg attatttgat    4800
taatttgtat tttttccaat agactaagct tggtgagttg ggacagtatt ttttttcatg    4860
attataccc cagagtctag tcttcaatca taaccagaaa actgcaaggg aaagtattta     4920
acatctaacc aaattaatat aaaataaaaa atgaagtcat ttagtgtagg tgagatagtg    4980
ctaaaataga taaataaact tgtagtgtct tcacatagca ggtactatag aaaaggtcaa    5040
attctttggc tagtcttgta aaatttgttt ttaaccaaag ggggaagaag tctatatttt    5100
cagaggtgtt catcacagaa ttagctgtaa taactaaaga aaaccctgac atatcaccca    5160
tatgtccaat aatgaaagag tagtcagtaa attaacattg tgatgtttat atagacaata    5220
gaaaacattg tcaatataaa ctgaaaaaag cataataaac agttatattt atactacatt    5280
tgcaactaaa tgaacataat tataaatttg gacaaaggaa ggaggagtat ggcaagatga    5340
aaagaattgc tttaaggttt atatatgttt ttattttttt aataatgcat tattttgtga    5400
ttttaaaaag ttactgtcgt agtgttgcat attttttgta acatcactat atgtactttt    5460
```

```
ctcttttag  tatggacctg  tatttagttt  taccatggta  ggcaagacat  ttacttacct  5520
tctggggagt  gatgctgctg  cactgctttt  taatagtaaa  aatgaagacc  tgaatgcaga  5580
agatgtctac  agtcgcctga  caacacctgt  gtttgggaag  ggagttgcat  acgatgtgcc  5640
taatccagta  ggtgacactg  ttaccataaa  taaagacaaa  tctatacctc  agtagttata  5700
gctaatagtg  agacattata  catttaaaat  gtagaaacag  ccaggcatgg  tggctcattc  5760
ctgtaatccc  agcactttgg  gaggccaagg  tgggtggatc  actcaaagtc  aggagttcaa  5820
gaccagcctg  gccaacatgg  tgaaaccctg  tctctactaa  aaatacaaaa  attagctggg  5880
tggggctggt  ggtgcacacc  tgtaaattcc  agctacttgg  gaggctgagg  catgagaatc  5940
gcttgaaccc  aggaggcgga  ggttgcagtg  agccgagatc  acaacactgc  actttagcct  6000
tggcaacaga  gtgagaccct  gtctcaaaaa  cagaaacaaa  aaaccaaaca  cacacacaca  6060
cacgcacgcg  cacacacaca  cacacacaca  cacacacaga  aaccaaccaa  acaaaaatgt  6120
aataaaatgt  agaaccagtt  tattccttgg  ttcaaaagtc  tgaagaatca  tgagaagaaa  6180
ggccatggat  aactgataag  taatgggtat  ttagttttat  atttgctgtc  atggctaaac  6240
aatattaaag  ggcttcctgt  acaaataatg  gaatcaatga  taacttagca  tactgggatt  6300
taatttgaaa  gggttattag  acaatgctgt  tacttcatca  aaaggacttc  ctgcctaccc  6360
attcctgcct  gaaattctaa  cataagcgct  gtttagagat  tgctgacttc  agaagtcctc  6420
ttttaatgca  acaacttcac  gtgtggggta  catctatgtg  tatgttttac  cctcaaaagc  6480
caaatacgaa  attgttttaa  gttgatatag  aacacaaatc  agacaattgg  ccccaatgct  6540
tggtatgggc  tctggctgtg  aatgtaacac  acattagcca  gtaccctagt  atagcagtta  6600
agagttaaca  ttaaatcttg  tttctagtga  tggggaatga  gggaatgaat  gcctctcctt  6660
aaggccaaaa  aacagggccc  tggaaaatcc  ctctgttcag  atatatatat  tcatttagac  6720
tctattcatt  tagagtcaga  tagatctatt  catttagact  cttaaaatgt  aaatgcccaa  6780
agggttaaaa  ccattacttg  tgttagtgtt  acataattat  aataacctaa  atggatttta  6840
tgataaaaca  aaaatgtgtt  ttaatgccgt  atccccgttt  tgaattttt  tgaaggtttt  6900
cttggagcag  aagaaaatgt  taaaaagtgg  ccttaacata  gcccacttta  aacagcatgt  6960
ttctataatt  gaaaaagaaa  caaaggaata  ctttgagagt  tggggagaaa  gtggagaaaa  7020
aagtaagcaa  aatgttttat  gtttgtccta  acatttctac  ttctctgtga  atagaaaagt  7080
agagtatata  tgtgtgtagt  atataaaaaa  caaattacag  tgtatgtaaa  actaccttag  7140
atttatggga  gggttatgta  atgattacca  tgaagttgta  actgagaatc  cagttttat  7200
actgggctgc  aagttaagta  ttgccttcag  aagcaattgc  tgtgcccata  gtaggaagca  7260
acatctgccc  acagggcagc  aggacccagg  gcagcaggtc  actatattct  gggtctggcc  7320
tttggcctct  gtaagagttc  cagaatcttt  gttttggta  tacttaagtt  gatattgata  7380
tattttctaa  ccatacaaga  aactgatgta  taaattagaa  tgccaatgta  ataatgcatg  7440
tgagacatat  aattacagca  ccaagaaatc  cagaatattt  actgatattc  ttttattga  7500
caaatataat  tggaaagcca  gatgatcatt  ggaagttcat  ttagtgaatg  tggaattaac  7560
aggaaattaa  ttgataatt  tttattagtt  gtcatcaaat  tatgcttgcc  tggtgcattt  7620
gtctccagtg  ttgggatata  ctaattggtg  attatagttt  tctttacat  atcgccagta  7680
attccatttt  ggccctgatc  ttcctacttt  taacctggga  ataatctga  tctttggcta  7740
ctattccttg  ggaagtacct  tattattgtc  atatgcacta  taaataaccct  tttttctgct  7800
```

-continued

```
tttgttattg tgacctggaa atcaaataac cacatttatt ctttttcatga tgaagtgctc    7860
atgagtgggg ttttgagatg tgtttctggg atctgttttg gctgtttaga gggacagggt    7920
gcttcacatt gtttggttta ttgcccctct ttgttgttgt acatagtcac atgtctgtct    7980
acagactttt tttgatgata tgaataggat cttgtttctt cttgagttct gttttttaatt    8040
ctcaattttc tttcactttt tggaaatagt aatgagaata atctttttt tctccctaga    8100
tgtgtttgaa gctcttttctg agctcataat tttaacagct agccattgtt tgcatggaaa    8160
ggaaatcaga agtcaactca atgaaaaggt agcacagctg tatgcagatt tggatggagg    8220
tttcagccat gcagcctggc tcttaccagg ttggctgcct ttgcctagtt tcaggtatgg    8280
ataaagaata tattcacacta ggttatttaa ctttgtataa ttattgtagt gttggtatgc    8340
tttgccttaa caaagataaa aattaaacaa gtaaaacata caaaatgggt aagattatga    8400
atcccctttc ttctataaga attcaagaca aattttcttt atataatgag ctcatttaaa    8460
gtaagtttca gttattaaa aaggtgattt gttgtctgtc tagtctaata ttttatttat    8520
gtttttgttt ttgagatgga gtcttgctct gttgccccag ctgtagtgca gtggtgtgat    8580
ctcggctcac tgcagtctct gcctcctgtg ttcaagcaat tctcctgcct catcctcctg    8640
agagctggga ctacaggcac gtgccaccat gcccaactaa ttttttctatt tttagtagag    8700
acagggtttc atcatgttgg ccaggctggt ttcaaactcc tgacctcagg tgatccacct    8760
gcctcagcct cccaaagtgt taggattaca ggcgtgagcc actgagccca gcctagttta    8820
aaagcctgct tacctcacgt attccttatc ctcaggaaag tctctgaact atacctaaaa    8880
gtgatacagc tcttctctag cacttgtttg aaatctttgg tggcttttta ttgtattgtg    8940
aagtttcttt gttttaaata tttgtgcctt tatttaattt tctgtttctt aaggacaggg    9000
actgcctctg atataaagaa atattgctct taggacttga tctatagctt agtgcttagt    9060
gttttgcata ttagtaggct ttctgtactt ttgttgattt attggtgttt aggtgacaga    9120
tggggaggag atagattgct agtccctttt cttctatttc tgccccctct atctagttac    9180
agattggaag aggggtggga gtaaaaggaa gagccaggag agattcccta aagttctctg    9240
gaactcatca taccttatat ttgcaaggag ctttgcagtt tcaaaatgtt ttcatatatc    9300
ttatattaga acacccagca cagccctgga ctcatagtgg ttctccata aatgtgcatt    9360
tctttttttt tttttttttt ttggtgatgg agtcttgctc tctcgcccag gctggagtgc    9420
agtggcatga gctcggctca ctgcaagctc tgcttccag gttcacgcca ttctcctgcc    9480
tcagcctccc gagtagctgg gactacaggc acccgccacc aagcctggct aattgttttg    9540
tactttttagt agagatgggg tttcaccgtg ttagccagga tggtcttgat ctcccgacct    9600
tgtgatccgc ccgcctcggc ctcccatagt gctgggatta caggcgtgag ccactgcacc    9660
tggcccataa atgtacattt ctacctgcct gtttctacct gctctgtctc ttggatgaag    9720
tcagagcttg ctatgttagg cccttcacat tctggcccag tctttctttc ttctactcat    9780
accaactaat ttaaccagat tattcaattc actttcttaa acaggcctat gttttcctgg    9840
ttcgactgta ttcatacagt taagccccaa catcttctct tctgtacaca tggtttcagt    9900
tgatcctcaa taacagatta acagtcttgt aaatgaaaca gagtaggagt ttttttttaga    9960
aggcttgatt taagaggggg cttgggagtc agactgccta gttttaaatt ccagctccaa    10020
tgtttgcttt ctgtgtgatc ttatgcagct agctataact tgaggttaat agtatgtacc    10080
tcacaggaag ataaaagtga gtaattcatg taaaacactt aacatggtac ctgctacata    10140
gtgaacatac tatttaaagg taaagtttag gagttgaagc ttgttttctg aatctgctag    10200
```

```
tattttcacc ccctacaaaa aactattgta ttagaaagtg aaaagtagaa ccagattcca    10260
tggaagaacc agagtgactc ttctgcttta agacttgatt tggtattaaa attggaattt    10320
tatgttaatt taaaagagta tcctactttc tgttgaactg gaaaatactt ctaaaggaat    10380
ttcttgcttg ttttaggcct ttagtttgaa cacaggcaat gtgttaagaa tctgggatat    10440
atatgttaaa taaagcacag ttcttgccct tagggactat ggacattttt aacaatgtaa    10500
gattttcatg acttccagta tgttcctggt tctgattttt ttgtcaatta ttttagagtc    10560
attaaagttg gttaaataag atgctttatg ctcggtcctg gttctcaaaa tgaatttgat    10620
cctagaaggt tatttcttta tttaagaaaa tcatctttat cttttaatta cagacgcagg    10680
gacagagctc atcgggaaat caaggatatt ttctataagg caatccagaa acgcagacag    10740
tctcaagaaa aaattgatga cattctccaa actttactag atgctacata caagtaagag    10800
ctattcagat aacatattaa gctgaagcag gaaattacac attaaaacac agttaaatag    10860
tatttccagt taaaaacag tgatgctggc aaaataagtt ggtagctgtg atctttggac    10920
tctttaaatt gttgagacat aaactattgg catcctgtgt cttactgtaa tcccagtgac    10980
tgggtatggt aaaagtttgc taatgaactg taatggagtc ttttgtaatc aaaatcgttt    11040
tgtgctggtc tgtctcttcc ctaagagaaa aaaaactctt gacttgtgat agtcaaatat    11100
aagagaccac tatacctgaa aaatgtattc attatgacac tttatttaaa ggttgaggca    11160
tgaaatgtat ctgccaaaat gttaaatttg tgtctttggt tcattcctta gggatgggcg    11220
tcctttgact gatgatgaag tagcagggat gcttattgga ttactcttgg cagggcagca    11280
tacatcctca actactagtg cttggatggg cttcttttg gccagagaca aaacacttca    11340
aaaaaaatgt tatttagaac agaaaacagt ctgtggagag aatctgcctc ctttaactta    11400
tgaccaggtt tgttggattt tcagtttca ttgctgcctt atgactttga ggatctgtgg    11460
ctaattttta aaagggacaa tttgagattt tctatatact atagcttaaa ttgatcagct    11520
tctctatttt tagcaaattc cctataacct tacctaaaat atcttaatgt tattgcttct    11580
tgccattaag ctttatcaga tatgttttgg gttgatggct tagagatcct tggggatgtt    11640
tctttggtac ttacttcctc tgcttcaaag tctggcttct gtacatagag gatattatgt    11700
gcatgttgtg tgtcttatga agtgtagaag cctctgaatt acttagaatt ctgtatgtcc    11760
agagtggcct gggcatgagc agagacttct aaaagtagta gtagtagtag taatgaggac    11820
aagacattta caaatactac atgcaacttg ctgggtggaa aggaagagag gacaactcac    11880
tgcacaacct gacattccat cttggaagca aaccttggtg atgtcatctt cctgttatct    11940
tttgtgcttt tggtcctata ttaatatggc acattacact gattttcaga tgttaattgt    12000
attcctggga taaatcctac tttgtcatgg tgcatagttc tttctatatg ttactacata    12060
taaacttgct ggtgttttgt tgaggatttt tgcatctata ttcataaagg atattgatct    12120
ctagtttcac tgtgatgtct ttgactggtt ttgatatcag gatcatactc atctcataga    12180
atgtatttgg aagtattctt ttttcttct aatttttgga agagtttgtg gatgattggt    12240
gttaatcctt ttttacatat ttgcaaaaat tcagcagtga aatcatctag atctgtgctt    12300
ttctttctga gaagacttta cttactaatt caatttattt gttacaggtt tattcagata    12360
ttccatttct tcttatgtca gtttcagtag tttatatctc tctaggaatt tgtccatttc    12420
atctaggtta cctaatttgt tggcatacaa ttgttcatag tattctcata atccttttta    12480
tttctgtaag ctcagtagtg atgtctcaac actcattctt gttttagta acttaaaata    12540
```

```
acagcttaac tgatatattt acatagcata aatccatcca tttaaaatgt acactttgtg    12600 gttttttagca tattaagagt tgggaaacca tcatcataat ttaatttag aacatttaca    12660 tcactcccaa aagagagctg gtacccatta gcagtcatgc ttcattctcc ctgactgctg    12720
cccctggcaa ccattaatct ccttttgcct ctgtgagttt gcctattctg gatatttcat    12780
gtaaatggga tcatacaatt tgtagtcttt tgtgactacc ttgtttcact tagcatgtta    12840
tcagggttct tccatgttgt agcatgtatc agtacttcag tctttgttat taccaataat    12900
attccattat atggatagac cacattttgt ttatttgttc atcagttgat ggacatttga    12960
gttgttccca ccttttaaac tattatgaat aatgccgctc taaacgtttg tgtactgatt    13020
ttatgtggac atgtgttttc aattttgggg ggtcatacct aggagtagaa ttgctgggtt    13080
ataaggtaac tttgaagaac tgccagactg ttttaaaaag tggctgcacc actttcaaat    13140
ctcactaaac agtatatgtt ggtcctgact tcacccctc accaaacttg ttacttgatt    13200 ttttattat aataggtgtg aagtgatact tttttttttt ttttgagac agagtcttgg    13260 tgtgatgccc aggctctagt gcaatggcgc gaccttggct tactgcaacc tcggcttccc    13320
aggttcaagc tattctcctt cctcagcctc ccaagtagct gggtacacac caccacgcct    13380
ggctaatttt tgtattttg gtagagacaa ggttgtacca tattggccag ctggtcttg    13440 aactcctgac ctcaagtcat ctgcccgcct tggcctccca aagtgctggg attacaggtg    13500
tgagccacca tgcccagttg gtattttgtt ttgattttgc atttccctgg tgactagtga    13560
tgttgagtgt cttatgatgt gttctttggc tttggtatac ttctttggag aaatgtctgc    13620
tcacatcctg ttcccatatt taaaatgagt tgtcttttta ttattgagtt gtaagagttc    13680 atctatttt ttttaatgtg cttttggtgt cagagaaact aatgcctaat caaagtgtat    13740
gaagatttat ttctgtgtat tcttcttagt gttttgtagt ttcatatctt acatttaggt    13800
ctttgatcca ttatgaatta atttatgtat atgatgtgag gtcatcattc ttttgcatgt    13860
gtttatccag ttgtcccaca ctgtttgttg aaaagactat ttttccacg ttgaattgtc    13920 tttgtaaaaa aatctattat agccaggcgc agtggcacgt gcctgtattc tcagctactg    13980
agaagctgag atgggaaggt cgcttgagct caggacttgg ggtccagcct gggcaacata    14040
gcgaaaccct gtctctgaaa aataaaatac attttaaaaa gcctcttgac cataaattta    14100
aggctttatt tctggactca gttctattcc attgatatgt ttagtctgat gccattacgt    14160
agttttgtaa taagttttga attcgggagt gtgagtcctc tgactttgtc cttttcaagg    14220
ctgtttatct actcctagtc cctttagttt ccatatgaat tttggggtca gtgtgtcagt    14280
ttctgcaaag aagctagctg agatttttga caatgattgc attgtatcgc catattaatt    14340
tgggagcaca attttagtct ttaaatctgt gaacatgaga tgtctttctc ttattttagt    14400
tctttaattt ctttcaacaa tgttttatag ttttggtgc acaatgttta aacttctctt    14460
gttaaatgta ttcttaagta ttttattatt gttattttt tgatgttatt ctttcttctg    14520
ccagtccaaa tctgctgttg atccctcgg gtgaattttt catttcagtt ctcatacttc    14580
tcagttcttg aatttctatt tggttctcta aaaaaataat atattgatat tctccatttt    14640
actagagata tctaggcata ttttgctata gttctttgaa cctgtttata atagctgatt    14700
taaattcatt atctagtaag tccaatgtct gggcttcttc atggatagtt tctattaaac    14760
tgcttgcttt ttctatgtac tggccatact ttcctgtttt ggtgtgtttt ttgtaatttt    14820
tttgttgaaa actgtacatt taaaataatg tggcaactgt ggaaatcaga tgccctcctc    14880
cctgggttta ttgttgctgg ctcttttgttg ttgttgttgt tgctgctgct gtttgtttac    14940
```

```
tgcgtttcct ggattaatta tgtcattcct tgttcagtga ggtcactgaa atctctgctt    15000
gcttacttta gtgggcatct aatatttgga cagagattta ctgaagtgct ttgaacagcc    15060
agtctcctag cttttgctga aaggctctgt atgtgtgtgt tagggatgt tattaacact     15120 ccaacaggca gttacaagtc tgccttcact acctgtgtgt acaggtcagc cagaggtaaa    15180
agattacagc ctcttagatc ttacctgggc atatgcatgg tcttatacat atgtgtggcc    15240
ttcaagattc tcttatgttg gaacttttca aagtctcctg tggacatctt actccccagt    15300
tttccctttt aaacttcttg ttctgtctct tagcaccaac tgatatcacc atctcaggcg    15360
ccttcagtgt taaacaattt ttgctaaata tttttggaaa atttgctctg gctcctctaa    15420
tagttgttag gcttctggct ttcacagctg ctatagttgt catgctgttg gtttccgggg    15480
ctaccatgga tttggggaga ggaggatgaa agaaatacaa cttacactac cacaaagctt    15540
actcttctta ccaagattca gatttctttt tcttgaatta actctcctta gattgttgca    15600
agcctttggt taatcttcca gaattttgaa aaagttgaca ttaagattgt tgctactgtt    15660 ttcattttt ggaggagtga attttgtag gttcttactt cattcttcag ggcaatcgct      15720
tctgttacct tgccctcctt tttcaccatg gacagtggta gagcatgata accccagcca    15780
ccctgaacca gttacctctg tacttttagc tggaatgcaa gctgtcttgt actaactaag    15840
aagtaaaact aatttttttgt actgttgaag tatgttattt ataacaatca ggaaatgctt   15900
tctcatttta gctcaaggat ctaaatttac ttgatcgctg tataaagaa acattaagac     15960 ttagacctcc tataatgatc atgatgagaa tggccagaac tcctcaggtg agtatcttgg    16020
ctacatcttc ccctctatac ccccagtttt tatcaaaaag aagaaatagg tgggtgtggt    16080
ggttcacacc tgtaatctca cactttggg aggctgaggt gggaggatca cttgaggcca     16140
gaatttgaga ccagcctggg caacatagtg agactgacct catctctaca aaattttttc    16200
taaaaattag ctggccataa tggcacatgc ctgtggtccc agctgcttgg gaggctgatg    16260
tgggtagatt gcttgagcct gggaggttga aactgcagta atccatgatc acgccactgc    16320
attgctgcct gggcaacaga gcaagaccct gtctcaaaaa aaataaaaat aaaaagaaa     16380 gaaaagaaa agaggaagta gagtagcata aaagagattt ttttaaatta aaaaagtaga    16440
ataatcactt ctacctaatc ttcagttta tatactctaa aaacatattt ttacctaatt     16500
gtagatagta tacgtgctaa tctgtttttt ttttttttga gacggcattt cactcttgtt    16560
gcccaggctg gagtgcagtg gtgcgatctc agctcactgc aacctccgcc tcccgggttc    16620
aagcaattct tctgcctcag cctcccaagt agctgggatt acaggggcat gccaccatgc    16680
ctggctaatt ttttgtattt tagtagagat ggggtttatc catgttggtc aggctgatct    16740
cgaactcccg acctcaggtg atccaccgc cttggcctcc caaagtgctg ggattacagg     16800
tgtaatcccg cgcccggcct acatgctaat ctttaatgct aatcatgttc tgcattttc     16860 tttaacaatt gggttttaa aaatcaaagt acatattttt cttggtttta aaataacat      16920 tttgttgtaa aaaattgtta atatgaagtg tacaaattga tagtgaaagc ctctctgaaa    16980
ttccaaccct acctccaagg cattatgggt ttgatttgtg tactgtgtac ttccaaccca    17040
acgctggctc actggaaatc atcttgagtt aaaataattt ttagtttgcc tattatctag    17100
ccagttttta aatatatgta cagatggttc ttgatttatg tgattcaact tataattttt    17160
tgactttatg atggatttat caggatgtaa acctatcata agtcaaggag catctgagta    17220
tcccatgtat attcatgctt tattacacaa tgatctgatt atttgtcagc acattttaa     17280
```

```
attctctaat gaaatgtgtg gcttttgttt atagactgtg gcagggtata ccattcctcc    17340
aggacatcag gtgtgtgttt ctcccactgt caatcaaaga cttaaagact catgggtaga    17400
acgcctggac tttaatcctg atcgctactt acaggataac ccagcatcag gggaaaagtt    17460
tgcctatgtg ccatttggag ctggtaagat gattatattt tagattggaa atgtttgttc    17520
tgataacata tttgtctctg tcaaaatatt ccgaattgtg tttacaaatt atctctccct    17580
ttcctcatag ggacatttt gcaaactttt ttaggagaag aatctttata agttggagaa    17640
aaatatttcc tttgtaccaa atggaattgt tccataaatc cttatataat gcttcactac    17700
ttcctaacct gtctggtttt attaggtcta atttttatag aacatccttg ttttcccta    17760 caatggtatt taaagctctt tgtggattct cttttaaaga accattggag tcagcacacc    17820
attcagggaa taacagatta ctagcatttc acaaaaaagc aaaggcagtc tttaaaatt    17880 aaagctcttc tcgatcgtta gtcaacattt ttgctctctg aatatccgta tgagaaaatg    17940
gtctttaaat ttgggcaggt tgtgtgtagg cttgcaaatt tcatttccag taagatccta    18000
aaataattta gctataccct tgtttctcca gtaatttctc tgtccattgg ttctctgtac    18060
tgattaaact atattctatg ctttagtctt tccaaaggga tcatttaaat gacagatgac    18120
ttgtcattgg tcacactttt tccacatata aaggaaaata taaagtcctt tgggaacttc    18180
agatcttaac tttatgtaat aaatttaata ctgtggtgta taacacaata tataaaagaa    18240
tcatagtttt tttttttgaga gagtcttgct ctgtcaccca gtctggagtg cagtggcaca    18300
atctctcagc tcactgcaac ctccacctct gggttcaagt aattctcgtg ccttagcctc    18360
ctgagtagct gggattacag gtgtgtacca ccacgctcag ctaattttg agcttttagt    18420 agagactggg ttttgccatg ttggccaggc tggtctcgaa ttccaggctt gaagcaatct    18480
gcccaccttg gcctcccaca gtgctgggat tacaggcgtg agccatgcca cctggccaaa    18540
gaatcagatt gttaacagat gggaagagca ttagttctgt agcccaaatt ctgccccaaa    18600
gaggaatcgt ttctaaacta gtaattatct ggtttccact tgaactttac tagaaatggg    18660
ttgtgggttg ttcagttacc ttttatgatg gctcattcta tgtttggaca gctgtcattt    18720
ttagagcctt atgttaaagc tgaaatctgt ttctttttaa catctcattt atagttggtc    18780
ctaaccatag tctctgaact tatattgtat gaggtatttg agtacagata taatgtctcc    18840
tccatctttt tttcaatctt tgtgttagtt tcctagggct tctgtaacta attacaaatat   18900 gggtggctta aaacaataga aatatattct atcacagttt tggaggctgg aagtgtgaaa    18960
tcaaggtatt ggcaggaccg tgctcctcct taaggttcta caggagaatc cttccttgca    19020
tcttcctagc ttctggtggc tcttggcaac ccttggcttg taactacatt gttccaatta    19080
ctacccctgt cttcaacagg ctttcttctt gttcatgtct ctgtatctta acatggcatt    19140
cttataagga caccagtcat tggatctaag tcctacccta agtcagggtc atctcatctt    19200 aaataaattgt gtatataaag atcctatttc ccaattaaga tcacattcta aggttctgga    19260
tggacttgaa tttatgggg gatatatgat cttacgttaa tcttgttaaa tatcacatta    19320
catgtctcta atttctttac tcattctttt acctcgtaat tgtgctgttt atttatgttg    19380
gtgcatatag ttcattcatt ttcataatat tacattttgt gaatcatcag aatttatcta    19440
ctcttatgtt gattcaatta ggatacttct tgcttgttgc gattaaatcc ttggactatt    19500
cttcctgtaa gccaagcttc tctttagttg ttatatttga aatatggacc aatttgtaaa    19560
tgctcatctt aaatgtcact cctagaaata agtacagtta tgggccaagc aagcactgtg    19620
ctaagcacta tcagtttagg ttttttcttt tgatgaaaaa tcttgcaatg aaatgcccaa    19680
```

```
atcttaagtc aacattcatt gagttttgac aaatgaataa cctttagttt agtccaatgt   19740
atcaatcttt taaatggtta ttgcttcctg gccctgtctt aaaattttg cttagccct    19800 gagtcatgaa gatattctcc tgttcttctc tactgaaatt tatgctgtta gcatcatggt   19860
ttgtgaccct tcttgaatta gtatttgatt atggtgtgac ataggagttg aatttcattt   19920 ttccccatg taatatctag ttattcctgg accttatgtt gaaaagactt gcttttcctc    19980
attggcttgc tttggtgtct gtactgataa tcaaataacc ataaaatat tctgttctgg    20040 gctctctgct ctgttccatt gatctatttg ttgatcctta cctagtacca ctctgtttta   20100
tctttagtct tgaagtcaga tttgaaatca gttttatgtc ctccaactca gttcttttc    20160 caagattgct ttggatatcc taggtccttt gcattttat atgcatttta gaatcagctt    20220
gtcagtttct acatgggtgt gactttag tatattattt tgggttcatt aaatctcatt    20280
ttcttccata catttataat gacatttgag gtttgattgg aaggttttca tattgacttt   20340
taactagggc tttcttggga caaacagaat attctactat attcccaaac tagattacca   20400
tcttatgatt caaactttcc atatatttaa cccagatata tattttcaga aaaagtaatt   20460
ggaaaagtta tgtgatcagt caagtactgt tttcctaaaa tgtggtattg aaaatctcct   20520 ggaatttta ataattcatg ttgttttatg tgaaaagaat gtcatctttt tattatatta   20580
tctgtacatt tgctgttcat ctaaaatgta gataatatca ccccaggcta aaaggatga    20640 gaaagaattt aaactgattc ttataacttt ttctttttt tagggcgtca tcgttgtatt    20700
ggggaaaatt ttgcctatgt tcaaattaag acaatttggt ccactatgct tcgtttatat   20760
gaatttgatc tcattgatgg atactttccc actgtgaatt atacaactat gattcacacc   20820
cctgaaaacc cagttatccg ttacaaacga agatcaaaat gaaaaaggtt gcaaggaacg   20880
aatatatgtg attatcactg taagccacaa aggcattcga agagaatgaa gtgtacaaaa   20940
caactcttgt agtttactgt ttttttaagt gtgtaattct aaaagccagt ttatgattta   21000
ggattttgtt aactgaatgg ttctatcaaa tataatagca tttgaaacat tttctaatag   21060
ttatgatact tatacatgtg ctttcaggaa gttccttggt gaaacaattg ttgaggggg    21120 atctaggtaa ttggcagatt ctaaataata taatttccag atagtaattt taagagtact   21180
catcgctctt gccaaataag ttcagggtat tcaaatcttg gactagtcct gcaaggtata   21240
aagaataaaa atcccagtga gatacttgga aaccacagtt tattattatt tatctgggca   21300
attattgtgt gtgtgaggat ggaagggtag ggaataatcg aacatctaaa gccttgaata   21360
agagaatact aattgttttg gtatgatgat actcagaaat ggagatatta taggaaaaag   21420
aaatcctttg gaattttaac taaaatcact gcatatggga aattaagaga tccaggacca   21480
tatttgataa gagttcctaa aaataatgta attattaatg ctaaagactg ctcatgtatc   21540
ttgatctaat tactaaataa ttacatattt atttacctga taaatatgta tctagttcta   21600
caaggtcaca tttatgtgga agtccaaagt caagtcctta ggggataatt ttgttttggc   21660
tcagttgttc cctgcttcct tttttttttt tttttttga gatggagtct cgctctgttg   21720
cccaggctgg agtgcagtgg tgcgatctca gctcactgca tcctctgcct cccgggttca   21780
agcaattctc tgcctcagcc tcccaagtag ttgggattac aggcacctgc caccatgcct   21840
ggctaatttt ttgtattttt agtagagacg ggggtttcac tatgttggct aggctggtct   21900
tgaactcctg acctcgtgat ccacccgcct tggcctccca aagtgctggg attacaggca   21960
tgagccaccg cacctggcct tccctgcttc ctctctagaa tccaattagg gatgtttgtt   22020
```

| | | | | |
|---|---|---|---|---|
| actactcata | ttgattaaaa | cagttaacaa | acttttttct | ttttaaaatg tgagatcagt | 22080 |
| gaactctggt | tttaagataa | tctgaaacaa | ggtccttggg | agtaataaaa ttggtcacat | 22140 |
| tctgtaaagc | acattctgtt | taggaatcaa | cttatctcaa | attgtaactc ggggcctaac | 22200 |
| tatatgagat | ggctgaaaaa | ataccacatc | gtctgttttc | actaggtgat gccaaaatat | 22260 |
| tttgctttat | gtatattaca | gttcttttta | aaacactgga | agactcatgt taaactctaa | 22320 |
| ttgtgaaggc | agaatctctg | ctaattttc | agattaaaat | tctctttgaa aaaataca | 22378 |

<210> SEQ ID NO 3
<211> LENGTH: 1659
<212> TYPE: DNA
<213> ORGANISM: Homo sapiens

<400> SEQUENCE: 3

| | | | | | |
|---|---|---|---|---|---|
| gttcgttgca | acaaattgat | gagcaatgct | tttttataat | gccaactttg tacaaaaaag | 60 |
| ttggcatggc | ggcggcggct | gggatgctgc | tgctgggctt | gctgcaggcg ggtgggtcgg | 120 |
| tgctgggcca | ggcgatggag | aaggtgacag | gcggcaacct | cttgtccatg ctgctgatcg | 180 |
| cctgcgcctt | caccctcagc | ctggtctacc | tgatccgtct | ggccgccggc cacctggtcc | 240 |
| agctgcccgc | aggggtgaaa | agtcctccat | acattttctc | cccaattcca ttccttgggc | 300 |
| atgccatagc | atttgggaaa | agtccaattg | aatttctaga | aaatgcatat gagaagtatg | 360 |
| gacctgtatt | tagttttacc | atggtaggca | agacatttac | ttaccttctg gggagtgatg | 420 |
| ctgctgcact | gcttttaat | agtaaaaatg | aagacctgaa | tgcagaagat gtctacagtc | 480 |
| gcctgacaac | acctgtgttt | gggaagggag | ttgcatacga | tgtgcctaat ccagttttct | 540 |
| tggagcagaa | gaaaatgtta | aaagtggcc | ttaacatagc | ccactttaaa cagcatgttt | 600 |
| ctataattga | aaaagaaaca | aaggaatact | ttgagagttg | gggagaaagt ggagaaaaaa | 660 |
| atgtgtttga | agctctttct | gagctcataa | ttttaacagc | tagccattgt ttgcatggaa | 720 |
| aggaaatcag | aagtcaactc | aatgaaaagg | tagcacagct | gtatgcagat ttggatggag | 780 |
| gtttcagcca | tgcagcctgg | ctcttaccag | gttggctgcc | tttgcctagt ttcagacgca | 840 |
| gggacagagc | tcatcgggaa | atcaaggata | ttttctataa | ggcaatccag aaacgcagac | 900 |
| agtctcaaga | aaaaattgat | gacattctcc | aaactttact | agatgctaca tacaaggatg | 960 |
| ggcgtccttt | gactgatgat | gaagtagcag | ggatgcttat | tggattactc ttggcagggc | 1020 |
| agcatacatc | ctcaactact | agtgcttgga | tgggcttctt | tttggccaga gacaaaacac | 1080 |
| ttcaaaaaaa | atgttatta | gaacagaaaa | cagtctgtgg | agagaatctg cctcctttaa | 1140 |
| cttatgacca | gctcaaggat | ctaaatttac | ttgatcgctg | tataaaagaa acattaagac | 1200 |
| ttagacctcc | tgtaatgatc | atgatgagaa | tggccagaac | tcctcagact gtggcagggt | 1260 |
| ataccattcc | tccaggacat | caggtgtgtg | tttctcccac | tgtcaatcaa agacttaaag | 1320 |
| actcatgggt | agaacgcctg | gactttaatc | ctgatcgcta | cttacaggat aacccagcat | 1380 |
| cagggaaaa | gtttgcctat | gtgccatttg | gagctgggcg | tcatcgttgt attggggaaa | 1440 |
| attttgccta | tgttcaaatt | aagacaattt | ggtccactat | gcttcgttta tatgaatttg | 1500 |
| atctcattga | tggatacttt | cccactgtga | attatacaac | tatgattcac acccctgaaa | 1560 |
| acccagttat | ccgttacaaa | cgaagatcaa | aatgcccaac | tttcttgtac aaagttggca | 1620 |
| ttataagaaa | gcattgctta | tcaatttgtt | gcaacgaac | | 1659 |

<210> SEQ ID NO 4
<211> LENGTH: 85

```
<212> TYPE: DNA
<213> ORGANISM: Homo sapiens

<400> SEQUENCE: 4
aaucuaggag gcaggugcuc acuuguccuc cuccaugcuu ggaaaaugca gggaggaggc        60
cauaguggca acuguuacca ugauu                                              85
```